(12) United States Patent
Kawamoto et al.

(10) Patent No.: US 10,717,852 B2
(45) Date of Patent: Jul. 21, 2020

(54) ADDITIVE FOR RESINS

(71) Applicant: KAO CORPORATION, Tokyo (JP)

(72) Inventors: Koichi Kawamoto, Wakayama (JP);
Motoi Konishi, Wakayama (JP);
Toshihiro Yano, Izumisano (JP);
Hayato Yoshikawa, Tokyo (JP)

(73) Assignee: KAO CORPORATION, Tokyo (JP)

( * ) Notice: Subject to any disclaimer, the term of this patent is extended or adjusted under 35 U.S.C. 154(b) by 235 days.

(21) Appl. No.: 15/568,730

(22) PCT Filed: Apr. 22, 2016

(86) PCT No.: PCT/JP2016/062831
§ 371 (c)(1),
(2) Date: Oct. 23, 2017

(87) PCT Pub. No.: WO2016/171275
PCT Pub. Date: Oct. 27, 2016

(65) Prior Publication Data
US 2018/0142088 A1 May 24, 2018

(30) Foreign Application Priority Data

Apr. 24, 2015 (JP) ................................. 2015-089599
Apr. 22, 2016 (JP) ................................. 2016-086026

(51) Int. Cl.
| | |
|---|---|
| C08L 9/06 | (2006.01) |
| C08J 3/20 | (2006.01) |
| C07G 1/00 | (2011.01) |
| C08H 7/00 | (2011.01) |
| B60C 1/00 | (2006.01) |
| C08L 21/00 | (2006.01) |
| C08L 97/00 | (2006.01) |
| C12P 7/22 | (2006.01) |
| C12P 7/24 | (2006.01) |

(52) U.S. Cl.
CPC .................. *C08L 9/06* (2013.01); *B60C 1/00* (2013.01); *B60C 1/0016* (2013.01); *C07G 1/00* (2013.01); *C08H 6/00* (2013.01); *C08J 3/203* (2013.01); *C08L 21/00* (2013.01); *C08L 97/005* (2013.01); *C08J 2309/06* (2013.01); *C08J 2497/00* (2013.01); *C12P 7/22* (2013.01); *C12P 7/24* (2013.01)

(58) Field of Classification Search
CPC .......... C08L 9/06; C08L 21/00; C08L 97/005; C08J 3/203; C07G 1/00; C08H 6/00; B60C 1/00; B60C 1/0016
See application file for complete search history.

(56) References Cited

U.S. PATENT DOCUMENTS

| | | | | |
|---|---|---|---|---|
| 4,764,596 | A * | 8/1988 | Lora ................... | C07D 307/50 162/16 |
| 5,196,460 | A * | 3/1993 | Lora ...................... | C08L 21/00 524/72 |
| 7,064,171 | B1 | 6/2006 | Halasa et al. | |
| 2010/0204368 | A1 * | 8/2010 | Benko ....................... | B60C 1/00 524/73 |
| 2012/0302664 | A1 | 11/2012 | Kamada | |
| 2013/0197132 | A1 | 8/2013 | Fujikura | |

(Continued)

FOREIGN PATENT DOCUMENTS

| | | |
|---|---|---|
| CN | 102718995 A | 10/2012 |
| CN | 103387677 A | 11/2013 |
| EP | 3 059 274 A1 | 8/2016 |
| EP | 3 192 825 A1 | 7/2017 |
| JP | 2007-119739 A | 5/2007 |
| JP | 2011-190329 A | 9/2011 |
| JP | 2012-241158 A | 12/2012 |
| JP | 2013-155303 A | 8/2013 |
| JP | 2015-6998 A | 1/2015 |
| JP | 2016-60750 A | 4/2016 |
| WO | WO 2013/094398 A1 | 6/2013 |
| WO | WO 2014/046203 A1 | 3/2014 |

(Continued)

OTHER PUBLICATIONS

International Search Report for PCT/JP2016/062831 (PCT/ISA/210) dated Jul. 5, 2016.

*Primary Examiner* — Peter D. Mulcahy
(74) *Attorney, Agent, or Firm* — Birch, Stewart, Kolasch & Birch, LLP

(57) ABSTRACT

Provided are an abrasion resistance improver for inorganic filler-containing rubber composition capable of giving high abrasion resistance to a rubber composition containing an inorganic filler, a rubber composition containing the abrasion resistance improver for rubber composition, a tire using the rubber composition, and a method for producing the abrasion resistance improver for rubber composition. The present invention are concerned with [1] an abrasion resistance improver for inorganic filler-containing rubber composition, including, as an active ingredient, lignin having an aldehyde yield rate by alkaline nitrobenzene oxidation of 12% by mass or more; [2] a rubber composition containing the abrasion resistance improver as set forth above in [1], a rubber, and an inorganic filler; [3] a tire using the rubber composition as set forth above in [2]; [4] a method for producing an abrasion resistance improver for inorganic filler-containing rubber composition, including, as an active ingredient, lignin having an aldehyde yield rate by alkaline nitrobenzene oxidation of 12% by mass or more, the method including steps (A-1) to (A-3); and [5] a method for producing an abrasion resistance improver for inorganic filler-containing rubber composition, including, as an active ingredient, lignin having an aldehyde yield rate by alkaline nitrobenzene oxidation of 12% by mass or more, the method including steps (B-1) and (B-2).

19 Claims, No Drawings

(56) References Cited

U.S. PATENT DOCUMENTS

2015/0041083 A1    2/2015   Yoshikawa et al.

FOREIGN PATENT DOCUMENTS

| WO | WO 2015/056758 A1 | 4/2015 |
| WO | WO 2016/039213 A1 | 3/2016 |

* cited by examiner

ADDITIVE FOR RESINS

FIELD OF THE INVENTION

The present invention relates to an abrasion resistance improver for inorganic filler-containing rubber composition, a rubber composition containing the abrasion resistance improver for rubber composition, a tire using the rubber composition, and a method for producing the abrasion resistance improver for rubber composition.

BACKGROUND OF THE INVENTION

While rubber compositions are widely used for industrial applications, a use condition of molded articles using the rubber composition is becoming much more severe, and the development of a high-performance rubber material is a pressing need. For example, in a rubber composition which is used for a pneumatic tire of a car or the like, in order to enhance strength, abrasion resistance, fuel-saving property, and so on, compounded products of a filler, such as carbon black, silica, etc., are used for various purposes. For example, in the case of a tire rubber composition appealing a fuel-saving performance, a silica-based filler is compounded for the filler (see, for example, PTL 1).

CITATION LIST

Patent Literature

PTL 1: JP 2011-190329 A

SUMMARY OF THE INVENTION

The present invention is concerned with the following [1] to [5].
[1] An abrasion resistance improver for inorganic filler-containing rubber composition, including, as an active ingredient, lignin having an aldehyde yield rate by alkaline nitrobenzene oxidation of 12% by mass or more.
[2] A rubber composition containing lignin having an aldehyde yield rate by alkaline nitrobenzene oxidation of 12% by mass or more, a rubber, and an inorganic filler.
[3] A tire using the rubber composition as set forth above in [2].
[4] A method for producing an abrasion resistance improver for inorganic filler-containing rubber composition, including, as an active ingredient, lignin having an aldehyde yield rate by alkaline nitrobenzene oxidation of 12% by mass or more, the method including the following steps (A-1) to (A-3);
  Step (A-1); a step of subjecting a plant-based biomass to an enzymatic saccharification treatment to obtain a saccharification residue;
  Step (A-2); a step of subjecting the saccharification residue obtained in the step (A-1) to a heat treatment in a solvent including water and at least one selected from organic solvents having a solubility in water at 20° C. of 90 g/L or more, to obtain a heat treatment solution containing lignin; and
  Step (A-3); a step of subjecting the heat treatment solution obtained in the step (A-2) to solid-liquid separation to remove insoluble components, thereby obtaining the lignin.
[5] A method for producing an abrasion resistance improver for inorganic filler-containing rubber composition, including, as an active ingredient, lignin having an aldehyde yield rate by alkaline nitrobenzene oxidation of 12% by mass or more, the method including the following steps (B-1) and (B-2);
  Step (B-1); a step of treating a plant-based biomass with 8 parts by mass or more and 70 parts by mass or less of a basic compound and 10 parts by mass or more and 10,000 parts by mass or less of water based on 100 parts by mass of a solid component of the plant-based biomass under a condition in which an H-factor is 3,000 or less; and
  Step (B-2); a step of obtaining the lignin as a water-soluble component from the plant-based biomass having gone through the step (B-1).

DETAILED DESCRIPTION OF THE INVENTION

In a rubber composition, the fuel-saving property is improved through compounding with silica; however, since the silica does not have an affinity with organic rubbers and is hardly dispersed uniformly, a lowering of mechanical strength by insufficient distribution is liable to be caused, and an adhesive force of an interface between the silica and the rubber is weak, so that there is involved such a problem that the abrasion resistance is remarkably reduced. Then, in the rubber composition having silica compounded therein, a rubber composition having high abrasion resistance is required.

In response to this problem, in recent years, there is a technology of strengthening the adhesion of an interface between the silica and the rubber by using a silane coupling agent including a mercapto group or the like in a molecule whereof, however, the effect for improving the abrasion resistance is still insufficient. In addition, it may be considered that not only the addition of an inorganic filler, such as silica, etc., suppresses the reduction of the abrasion resistance, but also thinning of a tread is able to contribute to resource decrease, and therefore, the development of a rubber having excellent abrasion resistance is desired.

The present invention is concerned with an abrasion resistance improver for inorganic filler-containing rubber composition capable of giving high abrasion resistance to a rubber composition containing an inorganic filler, a rubber composition containing the abrasion resistance improver for rubber composition, a tire using the rubber composition, and a method for producing the abrasion resistance improver for rubber composition.

The present inventors have found a novel attribute that when a specified lignin is compounded in a rubber composition including an inorganic filler, the abrasion resistance of the rubber composition is enhanced.

Specifically, the present invention is concerned with the following [1] to [5].
[1] An abrasion resistance improver for inorganic filler-containing rubber composition, including, as an active ingredient, lignin having an aldehyde yield rate by alkaline nitrobenzene oxidation of 12% by mass or more.
[2] A rubber composition containing lignin having an aldehyde yield rate by alkaline nitrobenzene oxidation of 12% by mass or more, a rubber, and an inorganic filler.
[3] A tire using the rubber composition as set forth above in [2].
[4] A method for producing an abrasion resistance improver for inorganic filler-containing rubber composition, including, as an active ingredient, lignin having an aldehyde yield rate by alkaline nitrobenzene oxidation of 12% by mass or more, the method including the following steps (A-1) to (A-3):

Step (A-1): a step of subjecting a plant-based biomass to an enzymatic saccharification treatment to obtain a saccharification residue;

Step (A-2); a step of subjecting the saccharification residue obtained in the step (A-1) to a heat treatment in a solvent including water and at least one selected from organic solvents having a solubility in water at 20° C. of 90 g/L or more, to obtain a heat treatment solution containing lignin; and Step (A-3); a step of subjecting the heat treatment solution obtained in the step (A-2) to solid-liquid separation to remove insoluble components, thereby obtaining the lignin.

[5] A method for producing an abrasion resistance improver for inorganic filler-containing rubber composition, including, as an active ingredient, lignin having an aldehyde yield rate by alkaline nitrobenzene oxidation of 12% by mass or more, the method including the following steps (B-1) and (B-2);

Step (B-1); a step of treating a plant-based biomass with 8 parts by mass or more and 70 parts by mass or less of a basic compound and 10 parts by mass or more and 10,000 parts by mass or less of water based on 100 parts by mass of a solid component of the plant-based biomass under a condition in which an H-factor is 3,000 or less; and Step (B-2); a step of obtaining the lignin as a water-soluble component from the plant-based biomass having gone through the step (B-1).

In accordance with the present invention, an abrasion resistance improver for inorganic filler-containing rubber composition capable of giving high abrasion resistance to a rubber composition containing an inorganic filler can be provided. Furthermore, a rubber composition containing the abrasion resistance improver for rubber composition, a tire using the rubber composition, and a method for producing the abrasion resistance improver for rubber composition can be provided.

[Abrasion Resistance Improver for Rubber Composition]
[Lignin]

From the viewpoint of enhancing the abrasion resistance of the inorganic filler-containing rubber composition, the lignin which is used as the abrasion resistance improver for rubber composition of the present invention (hereinafter also referred to simply as "lignin") is one having an aldehyde yield rate by alkaline nitrobenzene oxidation of 12% by mass or more. Namely, the abrasion resistance improver for rubber composition of the present invention includes, as an active ingredient, lignin having an aldehyde yield rate by alkaline nitrobenzene oxidation of 12% by mass or more.

In natural lignin, three kinds of monomers of monolignol are bonded to each other through an enzymatic reaction to form a giant polymer. A main bond of this natural lignin is called a β-O-4 bond. In the lignin, decomposition of this β-O-4 bond and various condensation reactions between functional groups of lignin proceed in a process of extraction from a plant-based biomass, and the constitution of bonds in the lignin changes. It is known that the degree of structural change of the extracted lignin is expressed based on an aldehyde yield rate by alkaline nitrobenzene oxidation. The alkaline nitrobenzene oxidation is a method of decomposing the β-O-4 bond in the lignin and quantitating the amount of the β-O-4 bond from the produced aldehyde monomer. Namely, as for the aldehyde yield rate by alkaline nitrobenzene oxidation, the higher the value, the lower the degree of denaturation. The present inventors considered that in the lignin, the lower the denaturation, the higher the content of an aliphatic OH group or a phenolic OH group, and the higher the reactivity in the resin, and then conjectured that when low denatured lignin is used, the adhesiveness particularly between the inorganic filler and the rubber in the rubber composition can be improved, so that the abrasion resistance of the rubber composition can be improved.

From the viewpoint of giving abrasion resistance and fuel-saving property of the inorganic filler-containing rubber composition, the aldehyde yield rate of lignin by alkaline nitrobenzene oxidation is preferably 15% by mass or more, more preferably 16% by mass or more, still more preferably 17% by mass or more, yet still more preferably 18% by mass or more, even yet still more preferably 20% by mass or more, even still more preferably 20% by mass or more, and even still more further preferably 25% by mass or more. Then, though it may be considered that the higher the aldehyde yield rate, the more excellent the effects of the present invention, from the viewpoint of easiness of production, the aldehyde yield rate is preferably 60% by mass or less, more preferably 50% by mass or less, still more preferably 40% by mass or less, and yet still more preferably 30% by mass or less.

A method of measuring the aldehyde yield rate by alkaline nitrobenzene oxidation is according to the method described in the Examples of the present specification.

For example, from the viewpoint of obtaining low denatured lignin, the lignin having a specified aldehyde yield rate of the present invention can be obtained by regulating a decomposition/extraction condition from the plant-based biomass.

From the viewpoint of giving high abrasion resistance and fuel-saving property of the inorganic filler-containing rubber composition, a weight average molecular weight of lignin of the present invention is preferably 500 or more, more preferably 1,000 or more, still more preferably 1,200 or more, and yet still more preferably 1,500 or more, and preferably 30,000 or less, more preferably 12,000 or less, still more preferably 10,000 or less, yet still more preferably 8,000 or less, even yet still more preferably 5,000 or less, even still more preferably 3,000 or less, even still more further preferably 2,700 or less, and even yet still more further preferably 2,200 or less.

A method of measuring the weight average molecular weight of lignin is according to the method described in the Examples of the present specification.

From the viewpoint of obtaining low denatured lignin, the sulfur content in the lignin of the present invention is preferably 1% by mass or less, more preferably 0.8% by mass or less, and still more preferably 0.5% by mass or less. Then, from the viewpoint of economy, the sulfur content in the lignin is preferably 0.001% by mass or more, more preferably 0.005% by mass or more, and still more preferably 0.01% by mass or more.

A method of measuring the sulfur content is according to the method described in the Examples of the present specification.

For example, from the viewpoint of obtaining low denatured lignin, the lignin having the foregoing sulfur content can be obtained by regulating a decomposition/extraction condition from the plant-based biomass.

[Production Method]

The lignin that is the active ingredient of the present invention is preferably one obtained by the following method A or method B.

Method A:

Method A including the following steps (A-1) to (A-3).

Step (A-1); A step of subjecting a plant-based biomass to an enzymatic saccharification treatment to obtain a saccharification residue.

Step (A-2); A step of subjecting the saccharification residue obtained in the step (A-1) to a heat treatment in a solvent including water and at least one selected from organic solvents having a solubility in water at 20° C. of 90 g/L or more, to obtain a heat treatment solution containing lignin.

Step (A-3): A step of subjecting the heat treatment solution obtained in the step (A-2) to solid-liquid separation to remove insoluble components, thereby obtaining the lignin.
Method B:
Method B including the following steps (B-1) and (B-2).
Step (B-1); A step of treating a plant-based biomass with 8 parts by mass or more and 70 parts by mass or less of a basic compound and 10 parts by mass or more and 10,000 parts by mass or less of water based on 100 parts by mass of a solid component of the plant-based biomass under a condition in which an H-factor is 3,000 or less.
Step (B-2); A step of obtaining the lignin as a water-soluble component from the plant-based biomass having gone through the step (B-1).

Items which are common in the methods A and B are hereunder described.
<Plant-Based Biomass>
Examples of the plant-based biomass include a herbaceous biomass and a woody biomass. Of these, a herbaceous biomass is preferred.

The herbaceous biomass means a plant raw material growing on the grassland, exclusive of trees, or a non-woody plant part. Specifically, examples thereof include gramineous, malvaceous, and leguminous plant raw materials; and non-woody raw materials of palmaceous plants.

Examples of the gramineous plant raw material include bagasses, such as sugar cane bagasse, sorghum bagasse, etc., switchgrass, elephant grass, corn stover, corn cob, rice straw, wheat straw, barley, Japanese pampas grass, lawn, Johnson grass, Erianthus arundinaceus, and napier grass. Examples of the malvaceous plant raw material include kenaf and cotton. Examples of the leguminous plant raw material include alfalfa. Examples of the non-woody raw material of palmaceous plant include palm hollow bunch.

Among those, from the viewpoints of productivity and handling property, gramineous plant raw materials are preferred; sugar cane bagasse, corn cob, or rice straw is more preferred; sugar cane bagasse is still more preferred.

Examples of the woody biomass include various timbers, such as various wood chips obtained from conifers, e.g., Japanese larch, Japanese cedar, etc., or broadleaf trees, e.g., oil palm, Japanese cypress, etc.; wood pulps obtained from these timbers; and the like.

These plant-based biomasses may be used alone or in combination of two or more thereof.

Though the plant-based biomass may be used without being subjected to a milling treatment, from the viewpoint of treatment efficiency, the plant-based biomass is preferably subjected to a milling treatment.

A milling device to be used is not particularly limited, and examples thereof include roll mills, such as a high-pressure compression roll mill, a rotating roll mill, etc.; vertical roller mills, such as a ring roller mill, a roller-race mill, a ball-race mill, etc.; tank-drive medium mills, such as a tumbling ball mill, a vibration ball mill, a vibration rod mill, a vibration tube mill, a planetary ball mill, a centrifugal fluid mill, etc.; medium agitating mills, such as a tower-type mill, an agitating tank mill, a flow tank mill, an annular mill, etc.; consolidated shear mills, such as a high-speed centrifugal roller mill, an Angmill, etc.; a mortar; a stone grist mill; a Masscolloider; a fret mill; an edge runner mill; a knife mill; a pin mill; a cutter mill; and the like.

Among those, from the viewpoints of milling efficiency of a plant-based biomass and productivity, tank-drive medium mills or medium agitating mills are preferred; tank-drive medium mills are more preferred; vibration mills, such as a vibration ball mill, a vibration rod mill, a vibration tube mill, etc., are still more preferred; and a vibration rod mill is yet still more preferred.

The milling method may be conducted in either a batch-wise or continuous manner.

The material of the apparatus and/or medium to be used for milling is not particularly limited, and examples thereof include iron, stainless steel, alumina, zirconia, silicon carbide, silicon nitride, glass, and the like. From the viewpoint of milling efficiency of the cellulose-containing raw material, iron, stainless steel, zirconia, silicon carbide, or silicon nitride is preferred; and from the viewpoint of industrial use, iron or stainless steel is more preferred.

From the viewpoint of milling efficiency of the plant-based biomass, it is preferred that the apparatus to be used is a vibration mill, and the medium is a rod or a ball.

In the case where the medium is a rod, from the viewpoint of efficient milling, an outer diameter of the rod is preferably 5 mm or more, more preferably 10 mm or more, and still more preferably 20 mm or more; and from the same viewpoint, it is preferably 100 mm or less, more preferably 50 mm or less, and still more preferably 40 mm or less.

In the case where the medium is a ball, from the viewpoint of efficient milling, an outer diameter of the ball is preferably 0.1 mm or more, and more preferably 1 mm or more; and from the same viewpoint, it is preferably 100 mm or less, and more preferably 50 mm or less.

Though a suitable range of a filling rate of the medium varies depending upon the type of the vibration mill, from the viewpoint of efficient milling, it is preferably 10% by volume or more, more preferably 30% by volume or more, and still more preferably 50% by volume or more; and preferably 95% by volume or less, more preferably 90% by volume or less, and still more preferably 70% by volume or less. The filling rate as referred to herein means a volume of the medium relative to the volume of the tank of an agitating part of the vibration mill.

Though a milling time varies depending upon the milling device to be used, the quantity of energy to be used, or the like, from the viewpoint of microfabrication of the plant-based biomass, it is generally one minute or more, and preferably 3 minutes or more, and from the viewpoints of microfabrication of the plant-based biomass and economy, it is generally 12 hours or less, preferably 3 hours or less, more preferably one hour or less, and still more preferably 12 minutes or less.

In addition, from the viewpoints of improvement of milling efficiency of the plant-based biomass, improvement of saccharification rate, and improvement of production efficiency (shortening of production time), it is preferred that the plant-based biomass is subjected to a milling treatment in the presence of a basic compound. After the treatment, it is preferred that the resultant is neutralized with an acid.

Examples of the basic compound which is used for the milling treatment include an alkali metal hydroxide, such as sodium hydroxide, potassium hydroxide, lithium hydroxide, etc.; an alkaline earth metal hydroxide, such as magnesium hydroxide, calcium hydroxide, etc.; an alkali metal oxide, such as sodium oxide, potassium oxide, etc.; an alkaline earth metal oxide, such as magnesium oxide, calcium oxide, etc.; an alkali metal sulfide, such as sodium sulfide, potassium sulfide, etc.; an alkaline earth metal sulfide, such as magnesium sulfide, calcium sulfide, etc.; a quaternary ammonium hydroxide, such as tetramethyl ammonium hydroxide, tetrabutyl ammonium hydroxide, etc.; and the like. Among those, from the viewpoint of improvement of enzymatic saccharification rate, the basic compound is preferably an alkali metal hydroxide or an alkaline earth metal hydroxide, more preferably an alkali metal hydroxide, and still more preferably sodium hydroxide or potassium hydroxide. These basic compounds can be used alone or in combination of two or more thereof.

Assuming that all of holocelluloses in the plant-based biomass are cellulose, from the viewpoint of improving the saccharification efficiency in the step (A-1) as mentioned later, the amount of the basic compound which is used from the milling treatment is preferably 0.01 molar times or more, more preferably 0.05 molar times or more, and still more preferably 0.1 molar times or more per mole of an anhydroglucose unit that constitutes the cellulose (hereinafter also referred to as "AGU"); and from the viewpoint of neutralization and/or washing easiness of the basic compound as well as the viewpoint of costs of the basic compound, it is preferably 10 molar times or less, more preferably 8 molar times or less, still more preferably 5 molar times or less, and yet still more preferably 1.5 molar times or less.

The water content at the time of milling treatment is preferably 0.1% by mass or more, more preferably 0.5% by mass or more, still more preferably 1% by mass or more, and yet still more preferably 2% by mass or more, and preferably 40% by mass or less, more preferably 30% by mass or less, and still more preferably 20% by mass or less relative to the dry mass of the plant-based biomass. When the water content at the time of milling treatment falls within the aforementioned range, the milling efficiency of the plant-based biomass as well as the mixing/permeation/diffusibility between the lignocellulose raw material and the basic compound is improved, and the saccharification treatment of the step (A-1) efficiently proceeds.

The water content at the time of milling treatment means the water content relative to the dry mass of the plant-based biomass, and it can be properly regulated by decreasing the water content included in the plant-based biomass or the basic compound by a drying treatment or the like, or increasing the water content by the addition of water at the time of milling treatment, or other means.

From the viewpoints of improvement of a yield rate of lignin and improvement of saccharification efficiency, an average particle diameter of the plant-based biomass obtained by the milling treatment is preferably 1 μm or more, and more preferably 5 μm or more, and preferably 150 μm or less, and more preferably 100 μm or less. The average particle diameter of the plant-based biomass is measured with a laser diffraction/scattering type particle size distribution analyzer "LA-950" (available from Horiba Ltd.).

From the viewpoints of improvement of a yield rate of lignin and improvement of saccharification efficiency, a cellulose I-type crystallinity of the plant-based biomass which is obtained after the milling treatment is preferably 0% or more, and preferably 40% or less, more preferably 30% or less, still more preferably 20% or less, and yet still more preferably 15% or less. The cellulose I-type crystallinity of the plant-based biomass is one calculated by the Segal method from a diffraction intensity value by the X-ray diffraction method and is defined according to the following calculation equation (1).

$$\text{Cellulose } I\text{-type crystallinity}(\%) = [(I_{22.6} - I_{18.5})/I_{22.6}] \times 100 \quad (1)$$

$I_{22.6}$ represents a diffraction intensity of a lattice plane (002 plane) (diffraction angle $2\theta=22.6°$) in the X-ray diffraction; and 118.5 represents a diffraction intensity of an amorphous part (diffraction angle $2\theta=18.5°$).

In the method B, the milling is not always adopted.

[Method A]

[Step (A-1)]

The Step (A-1) is a step of subjecting a plant-based biomass to an enzymatic saccharification treatment to obtain a saccharification residue.

From the viewpoints of improvement of saccharification efficiency, improvement of a yield rate of lignin, and suppression of denaturation of lignin, examples of the enzyme which is used for the saccharification treatment of the step (A-1) include a cellulase and a hemicellulase. These enzymes can be used alone or in combination of two or more thereof.

Here, the cellulase refers to an enzyme that hydrolyzes a glucoside bond of β-1,4-glucan of cellulose and is a generic term of enzymes called endoglucanase, exoglucanase or cellobiohydrolase, a β-glucosidase, and the like. As the cellulase which is used in the present invention, commercially available cellulase preparations and those derived from animals, plants, and microorganisms are included.

Specific examples of the cellulase include a cellulase preparation derived from *Trichoderma reesei*, such as Celluclast 1.5L (a trade name, available from Novozymes A/S), Cellic CTec2 (a trade name, available from Novozymes AIS), etc.; a cellulase derived from a *Bacillus* sp. KSM-N145 (FERM P-19727) strain; a cellulase derived from each strain, such as *Bacillus* sp. KSM-N252 (FERM P-17474), *Bacillus* sp. KSM-N115 (FERM P-19726), *Bacillus* sp. KSM-N440 (FERM P-19728), *Bacillus* KSM-N659 (FERM P-19730), etc.; cellulase mixtures derived from *Trichoderma viride, Aspergillus acleatus, Clostridium thermocellum, Clostridium stercorarium, Clostridium josui, Cellulomonas fimi, Acremonium celluloriticus, Irpex lacteus, Aspergillus niger,* or *Humicola insolens*; a heat-resistant cellulase derived from *Pyrococcus horikoshii*; and the like.

Among those, from the viewpoints of improvement of saccharification efficiency and improvement of a yield rate of lignin, a cellulase derived from *Trichoderma reesei, Trichoderma viride,* or *Humicola insolens*, for example, Celluclast 1.5L (a trade name, available from Novozymes A/S), TP-60 (a trade name, available from Meiji Seika Kaisha, Ltd.), Cellic CTec2 (a trade name, available from Novozymes A/S), Accellerase DUET (a trade name, available from Genencor International, Inc.), or Ultraflo L (a trade name, available from Novozymes A/S), is preferred.

In addition, specific examples of the β-glucosidase that is one kind of the cellulase include an enzyme derived from *Aspergillus niger* (for example, Novozyme 188 (a trade name, available from Novozymes A/S) and β-glucosidase, available from Megazyme International), an enzyme derived from *Trichoderma reesei* or *Penicillium emersonii*, and the like.

In addition, specific examples of the hemicellulase include a hemicellulase preparation derived from *Trichoderma reesei*, such as Cellic HTec2 (a trade name, available from Novozymes A/S), etc.; and a xylanase derived from *Bacillus* sp. KSM-N546 (FERM P-19729); and besides, a xylanase derived from *Aspergillus niger, Trichoderma viride, Humicola insolens,* or *Bacillus alcalophilus*; furthermore, a xylanase derived from a *Thermomy-* ces, *Aureobasidium, Streptomyces, Clostridium, Thermotoga, Thermoascus, Caldocellum,* or *Thermomonospora* genus; and the like.

From the viewpoints of improvement of saccharification efficiency and suppression of denaturation of lignin, the enzyme which is used in the step (A-1) is preferably one or more selected from the group consisting of the aforementioned cellulase and hemicellulase, more preferably one or more selected from the group consisting of cellobiohydrolase, a β-glucosidase, endoglucanase, and a hemicellulase, and still more preferably one or more selected from the group consisting of cellobiohydrolase and endoglucanase.

In the step (A-1), a treatment condition in the case of subjecting the plant-based biomass to an enzymatic saccharification treatment can be properly selected by the lignin content in the plant-based biomass, the kind of the enzyme used, and so on.

For example, in the case of using the aforementioned enzyme and using the plant-based biomass as a substrate, the saccharification treatment can be conducted by adding the enzyme in an amount of 0.001% (w/v) or more and 15% (w/v) or less to a substrate suspension of 0.5% (w/v) or more and 20% (w/v) or less and undergoing the reaction in a buffer solution having a pH of 2 or more and 10 or less at a reaction temperature of 10° C. or higher and 90° C. or lower for a reaction time of 30 minutes or more and 5 days or less.

It is preferred that the pH of the aforementioned buffer solution is properly selected according to the kind of the enzyme used. The pH is preferably 3 or more, and more preferably 4 or more, and preferably 7 or less, and more preferably 6 or less.

It is preferred that the aforementioned treatment temperature is properly selected according to the kind of the enzyme used. The treatment temperature is preferably 20° C. or higher, and more preferably 40° C. or higher, and preferably 70° C. or lower, and more preferably 60° C. or lower.

Furthermore, it is preferred that the aforementioned treatment time is properly selected according to the kind of the enzyme used. The treatment time is preferably 0.5 days or more, and preferably 3 days or less, and more preferably 2 days or less.

(Saccharification Residue)

By subjecting the plant-based biomass to an enzymatic saccharification treatment, the saccharification residue is obtained. Here, the saccharification residue refers to a solid component resulting from separation of the mixture after the enzymatic saccharification treatment by means of solid-liquid separation, such as centrifugation, etc. By washing this solid component with water several times, a water-soluble polysaccharide can be removed. Thereafter, the wet-state saccharification residue may be subjected to the next step (A-2), or the saccharification residue may be powdered by means of drying. From the viewpoint of improvement of production efficiency, it is preferred to subject the wet-state saccharification residue to the next step (A-2). In the case of undergoing the drying treatment, from the viewpoint of suppression of excessive denaturation of lignin, it is preferred to dry the saccharification residue at 100° C. or lower, and it is more preferred to subject the saccharification residue to freeze-drying.

[Step (A-2)]

The step (A-2) is a step of subjecting the saccharification residue to a heat treatment in a solvent including water and at least one selected from organic solvents having a solubility in water (hereinafter also referred to simply as "solubility") at 20° C. of 90 g/L or more, to obtain a heat treatment solution containing lignin.

From the viewpoint of obtaining low denatured lignin in a high yield rate, the solvent which is used in the step (A-2) is preferably a solvent including water and an organic solvent having a solubility in water at 20° C. of 90 g/L or more.

Though the water which is used in the step (A-2) is not particularly limited, examples thereof include distilled water, ion-exchanged water, pure water, and the like.

As for the organic solvent which is used in the step (A-2), from the viewpoint of easily separating the lignin from cellulose and a hemicellulose included in the saccharification residue (hereinafter also referred to simply as "lignin separability") to improve extraction efficiency of lignin, its solubility in water at 20° C. is preferably 90 g/L or more, preferably 100 g/L or more, and more preferably 120 g/L or more.

As for the organic solvent, from the viewpoint of improvement of extraction efficiency of lignin, its SP value is preferably 8 or more, and more preferably 9 or more, and preferably 23 or less, more preferably 16 or less, and still more preferably 13 or less. Here, the "SP value" means a solubility parameter and is determined by the Fedors method [Robert F. Fedors, Polymer Engineering and Science, 14, 147-154 (1974)].

From the viewpoints of lignin separability and improvement of extraction efficiency of lignin, the aforementioned organic solvent is preferably one or more selected from an alcohol, a nitrile, an ether, and a ketone.

Examples of the alcohol include methanol, ethanol, diethylene glycol, n-propanol, isopropanol, 2-butanol, isobutanol, t-butyl alcohol, and the like. Examples of the nitrile include acetonitrile and the like. Examples of the ether include dioxane and the like. Examples of the ketone include acetone, methyl ethyl ketone, and the like.

All of the above-exemplified organic solvents have a solubility in water at 20° C. of 90 g/L or more. These organic solvents can be used alone or in combination of two or more thereof.

Among these organic solvents, from the viewpoints of lignin separability and improvement of extraction efficiency of lignin as well as safety, one or more selected from ethanol, isopropanol, 2-butanol, acetonitrile, dioxane, acetone, and methyl ethyl ketone are preferred; one or more selected from ethanol, isopropanol, 2-butanol, and acetone are more preferred; and acetone is still more preferred.

From the viewpoints of lignin separability and improvement of extraction rate of lignin, a ratio of the organic solvent and water in the solvent in the step (A-2) [(organic solvent)/water] (mass ratio) is preferably 90/10 to 0/100, more preferably 90/10 to 0.01/99.99, still more preferably 70/30 to 10/90, and yet still more preferably 60/40 to 40/60.

In the step (A-2), from the viewpoint of improvement of a yield rate of lignin as well as the viewpoint of molecular weight control of lignin produced, it is preferred to further use an acid or a base, and it is more preferred to further use an acid.

Examples of the acid include inorganic acids, such as hydrochloric acid, sulfuric acid, nitric acid, phosphoric acid, boric acid, etc.; organic acids, such as p-toluenesulfonic acid (PTSA), trifluoroacetic acid, trichloroacetic acid, formic acid, acetic acid, citric acid, etc.; Lewis acids, such as aluminum chloride, a metal triflate, etc.; fatty acids, such as caprylic acid, pelargonic acid, capric acid, lauric acid, myristic acid, palmitic acid, stearic acid, oleic acid, linoleic acid, etc.; heteropoly acid; and the like. Among those, from the viewpoints of improvement of a yield rate of lignin and obtaining lignin with a low molecular weight, one or more selected from hydrochloric acid, sulfuric acid, phosphoric acid, PTSA, and aluminum chloride are preferred; one or more selected from hydrochloric acid and phosphoric acid are more preferred; and hydrochloric acid is still more preferred.

Examples of the base include the same materials as those useful as the basic compound in the aforementioned milling treatment. Among those, from the viewpoints of improvement of a yield rate of lignin and obtaining lignin with a high molecular weight, one or more selected from an alkali metal hydroxide and an alkaline earth metal hydroxide are preferred; an alkali metal hydroxide is more preferred; and one or more selected from sodium hydroxide and potassium hydroxide are still more preferred.

The aforementioned acid or base can be used alone or in combination of two or more thereof.

From the viewpoints of improvement of productivity and enhancement of decomposability of lignin, the use amount of the solvent in the step (A-2) is preferably 2 times by mass or more, more preferably 5 times by mass or more, still more preferably 10 times by mass or more, and yet still more preferably 15 times by mass or more, and preferably 40 times by mass or less, and more preferably 30 times by mass or less relative to the solid component of the saccharification residue.

From the viewpoints of lignin separability and improvement of extraction rate of lignin, the content of the organic solvent in the solvent in the step (A-2) is preferably 10% by mass or more, more preferably 30% by mass or more, and still more preferably 40% by mass or more, and preferably 90% by mass or less, more preferably 70% by mass or less, and still more preferably 60% by mass or less.

From the viewpoint of improvement of a yield rate of lignin as well as the viewpoint of molecular weight control of the produced lignin, the content of the acid or base is preferably 0.001% by mass or more, and more preferably 0.01% by mass or more, and preferably 1.0% by mass or less, and more preferably 0.5% by mass or less relative to the solvent in the step (A-2).

In the step (A-2), from the viewpoint of improvement of a yield rate of lignin, it is preferred to further use a radical scavenger.

From the viewpoint of improvement of a yield rate of lignin, the radical scavenger is preferably one or more selected from an aromatic radical scavenger, such as hydroquinone, benzoquinone, methoquinone, phenol, etc., an amine-based radical scavenger, an organic acid-based radical scavenger, a catechin-based radical scavenger, and molecular hydrogen; more preferably one or more selected from an aromatic radical scavenger and an organic acid-based radical scavenger; and still more preferably an aromatic radical scavenger.

From the viewpoints of suppression of excessive denaturation of lignin and improvement of a yield rate of lignin, a heat treatment temperature in the step (A-2) is preferably 80° C. or higher, more preferably 100° C. or higher, still more preferably 120° C. or higher, and yet still more preferably 150° C. or higher, and preferably 280° C. or lower, more preferably 250° C. or lower, still more preferably 220° C. or lower, and yet still more preferably 200° C. or lower.

From the viewpoints of suppression of excessive denaturation of lignin and improvement of a yield rate of lignin, a heating apparatus which is used in the step (A-2) is preferably an autoclave or a microwave heating apparatus.

From the viewpoints of suppression of excessive denaturation of lignin and improvement of a yield rate of lignin, a pressure at the time of heat treatment in the step (A-2) is preferably 0.1 MPa or more, and more preferably 0.5 MPa or more, and preferably 15 MPa or less, more preferably 10 MPa or less, still more preferably 5 MPa or less, and yet still more preferably 3 MPa or less.

A time of the heat treatment in the step (A-2) is not particularly limited and is properly selected according to the amount of the saccharification residue. From the viewpoints of suppression of excessive denaturation of lignin and improvement of a yield rate of lignin, the time is preferably 1 minute or more, more preferably 2 minutes or more, and still more preferably 10 minutes or more, and preferably 5 hours or less, more preferably 3 hours or less, still more preferably 2 hours or less, and yet still more preferably 1 hour or less.

[Step (A-3)]

The step (A-3) is a step of subjecting the lignin-containing heat treatment solution obtained in the aforementioned step (A-2) to solid-liquid separation to remove insoluble components, thereby obtaining the lignin.

As a method of obtaining the lignin, for example, in addition to solid-liquid separation, such as filtration, centrifugation, etc., steps of solvent removal by distillation, washing, drying, and so on can be properly combined. In the case of adding an acid or a base in the step (A-2), a step of undergoing neutralization is included. These steps can be conducted in the usual way. For example, there is exemplified a method in which the insoluble components are removed by means of solid-liquid separation of the heat treatment solution obtained in the step (A-2), the aforementioned organic solvent and water included in the liquid component are distilled off under reduced pressure, and the obtained residue is washed with water to obtain the lignin. When the residue after the solvent removal by distillation is washed with water, a water-soluble polysaccharide, etc. or salt, etc. can be removed, and the purity of lignin can be increased.

[Step (A-4)]

In the method A, a step (A-4) of taking out lignin with a low molecular weight from the lignin obtained in the aforementioned step (A-3) may be included. Examples of a method of taking out lignin with a low molecular weight include solvent fractionation, membrane separation with an ultrafiltration membrane, a reverse osmosis membrane, etc., and the like.

Examples of the step (A-4) in the solvent fractionation include a step of extracting the lignin in a solvent including water and at least one selected from organic solvents having a solubility in water at 20° C. of 80 g/L or more from the lignin obtained in the step (A-3). By undergoing the step (A-4), the weight average molecular weight of the obtained lignin can be regulated, and lignin with a low molecular weight is obtained.

As for the organic solvent in the foregoing step and the composition ratio of the foregoing solvent, the same as those in the aforementioned step (A-2) can be exemplified. The step (A-4) may be repeatedly conducted.

[Method B]

[Step (B-1)]

The step (B-1) is a step of subjecting a plant-based biomass to heat treatment with 8 parts by mass or more and 70 parts by mass or less of a basic substance and 10 parts by mass or more and 10,000 parts by mass or less of water based on 100 parts by mass of a solid component of the plant-based biomass within a range where an H-factor is 3,000 or less.

In the step (B-1), the basic compound (hereinafter also referred to as "alkali") is used.

Examples of the basic compound include an alkali metal hydroxide, such as sodium hydroxide, potassium hydroxide, lithium hydroxide, etc.; an alkaline earth metal hydroxide, such as magnesium hydroxide, calcium hydroxide, etc.; an alkali metal oxide, such as sodium oxide, potassium oxide, etc.; an alkaline earth metal oxide, such as magnesium oxide, calcium oxide, etc.; an alkali metal sulfide, such as sodium sulfide, potassium sulfide, etc.; an alkaline earth metal sulfide, such as magnesium sulfide, calcium sulfide, etc.; a quaternary ammonium hydroxide, such as tetramethyl ammonium hydroxide, tetrabutyl ammonium hydroxide, etc.; and the like. Among those, from the viewpoint of improvement of lignin rate, the basic compound is preferably an alkali metal hydroxide or an alkaline earth metal hydroxide, more preferably an alkali metal hydroxide, and still more preferably sodium hydroxide or potassium hydroxide. From the viewpoint of increasing a recovery rate of lignin as well as the viewpoint of workability such that the treatment can be conducted at ordinary temperature and atmospheric pressure, or the like, the basic compound is preferably sodium hydroxide.

From the viewpoint of increasing a recovery rate of lignin, the amount of the basic compound in the step (B-1) is preferably 70 parts by mass or less, more preferably 60 parts by mass or less, still more preferably 55 parts by mass or less, yet still more preferably 50 parts by mass or less, even yet still more preferably 40 parts by mass or less, even still more preferably 30 parts by mass or less, and even still more further preferably 20 parts by mass or less, and preferably 8 parts by mass or more, and more preferably 10 parts by mass or more based on 100 parts by mass of the solid component of the plant-based biomass.

From the viewpoint of increasing a recovery rate of lignin and the viewpoint of workability, such as uniform stirring and mixing, etc. as well as the viewpoint of economy regarding an excess of equipment, a heating cost, or the like, the amount of water in the step (B-1) is preferably 10 parts by mass or more, more preferably 150 parts by mass or more, still more preferably 250 parts by mass or more, yet still more preferably 350 parts by mass or more, even yet still more preferably 450 parts by mass or more, even still more preferably 550 parts by mass or more, even still more further preferably 650 parts by mass or more, and even yet still more further preferably 750 parts by mass or more, and preferably 8,000 parts by mass or less, more preferably 5,000 parts by mass or less, still more preferably 3,500 parts by mass or less, yet still more preferably 2,500 parts by mass or less, and even yet still more preferably 1,500 parts by mass or less based on 100 parts by mass of the solid component of the plant-based biomass.

As for the treatment of the step (B-1), from the viewpoint of increasing a recovery rate of lignin as well as the viewpoint of economy, the H-factor (hereinafter also referred to as "HF") is preferably 0.01 or more, more preferably 0.1 or more, still more preferably 1 or more, yet still more preferably 2 or more, and even yet still more preferably 3 or more, and preferably 3,000 or less, more preferably 1,500 or less, still more preferably 1,200 or less, yet still more preferably 1,000 or less, even yet still more preferably 400 or less, even still more preferably 300 or less, even still more further preferably 100 or less, even yet still more further preferably 50 or less, and even yet still more further preferably 30 or less.

The H-factor is one which has hitherto been used as a control index in a pulp cooking process and in which the effect of temperature and time is one variable.

In the treatment of the step (B-1), when the temperature is high, not only the reaction is promoted, but also the time is related thereto at the same time. Therefore, when the delignification reaction rate at 100° C. is defined as 1, a relative rate at other temperature is determined according to the Arrhenius equation, and the step (B-1) are calculated by the H-factor that is the product of the relative rate and a time at that temperature.

In the present invention, the H-factor (HF) is an index expressing a total amount of heat given in the reaction system by the treatment with an alkali of the biomass and expressed according to the following equation (2). HF is calculated by integrating a time t at which the biomass and the alkali solution come into contact with each other.

$$HF = \int_0^t \exp(43.2 - 16115/T) dt \quad (2)$$

Here, t is a time (h); T is an absolute temperature (K); and an integral range is 0 to t.

For example, in order that the H-factor may satisfy 3 or more, in the case of undergoing the heat treatment at 70° C., the treatment time of about 150 hours is required; in the case of undergoing the heat treatment at 85° C., the treatment time of about 20 hours is required; and in the case of undergoing the heat treatment at 100° C., the treatment time of about 4.5 hours is required.

From the viewpoints of a recovery rate of lignin, shortening of a cycle time, and economy, it is preferred that the temperature and time of the treatment of the step (B-1) are set up.

Accordingly, the temperature of the treatment of the step (B-1) is, for example, 10° C. or higher, and preferably 20° C. or higher; from the viewpoint of increasing a recovery rate of lignin as well as the viewpoint of shortening a cycle time, the treatment temperature is preferably 70° C. or higher, more preferably 80° C. or higher, still more preferably 90° C. or higher, and yet still more preferably 95° C. or higher; and from the viewpoints of a recovery rate of lignin and economy, the treatment temperature is preferably 180° C. or lower, more preferably 150° C. or lower, still more preferably 140° C. or lower, yet still more preferably 130° C. or lower, and even yet still more preferably 120° C. or lower.

The time of the treatment of the step (B-1) expresses a time maintained within the aforementioned temperature range of the treatment; and it is, for example, a time maintained within a temperature range of 10° C. or higher and 180° C. or lower, preferably a time maintained within a temperature range of 70° C. or higher and 150° C. or lower, more preferably a time maintained within a temperature range of 80° C. or higher and 140° C. or lower, still more preferably a time maintained within a temperature range of 90° C. or higher and 130° C. or lower, and yet still more preferably a time maintained within a temperature range of 95° C. or higher and 120° C. or lower.

The time of the treatment of the step (B-1) varies with a scale of the treatment equipment or a difference in temperature increase/decrease rate, and hence, it cannot be unequivocally defined. From the viewpoint of increasing a recovery rate of lignin, the treatment time is preferably 0.1 hours or more, more preferably 0.5 hours or more, still more preferably 1 hour or more, and yet still more preferably 1.5 hours or more. An upper limit of the treatment time is not particularly limited, and it is, for example, 1 month or less, and preferably 1 week or less. From the viewpoints of a recovery rate of lignin, shortening of a cycle time, and economy, the treatment time is preferably 50 hours or less, more preferably 28 hours or less, still more preferably 20 hours or less, yet still more preferably 15 hours or less, even yet still more preferably 10 hours or less, and even still more preferably 8 hours or less.

[Step (B-2)]

In the step (B-2), the lignin is, for example, obtained by taking out a water-soluble component after the foregoing treatment.

The foregoing water-soluble component can be taken out by, for example, separating a liquid part of the alkali-treated biomass. In addition to the aforementioned separation, it is preferred that the water-soluble component is taken out by a method in which the lignin existent in a solid part of the separated alkali-treated biomass is washed with water and then dissolved in water to achieve extraction. Furthermore, the basic compound may be removed from the obtained water-soluble component by using a dialysis membrane or the like.

[Step (B-3)]

In the method B, a step (B-3) of taking out lignin with a low molecular weight from the lignin obtained in the aforementioned step (B-2) may be included. Examples of a method of taking out lignin with a low molecular weight include solvent fractionation, membrane separation with an ultrafiltration membrane, a reverse osmosis membrane, etc., and the like.

Examples of the step (B-3) in the solvent fractionation include a step of extracting the lignin in a solvent including water and at least one selected from organic solvents having a solubility in water at 20° C. of 80 g/L or more from the lignin obtained in the step (B-2). By undergoing the step (B-3), the weight average molecular weight of the obtained lignin can be regulated, and lignin with a low molecular weight is obtained.

As for the organic solvent in the foregoing step and the composition ratio of the foregoing solvent, the same as those in the aforementioned step (A-2) can be exemplified. The step (B-3) may be repeated.

The lignin which is used in the present invention can be used as an abrasion resistance improver for inorganic filler-containing rubber composition. That is, when the lignin of the present invention is added to a rubber composition containing an inorganic filler, such as silica, etc., the abrasion resistance can be improved.

The abrasion resistance improver for rubber composition of the present invention can include, in addition to the aforementioned lignin, a known additive for rubber composition. In addition, if desired, the lignin is used through dilution with an oil, an ester compound, an organic compound which does not hinder the effects of lignin, or the like.

From the viewpoint of suitably obtaining the effects of the present invention, the content of lignin in the abrasion resistance improver for rubber composition of the present invention is preferably 50% by mass or more, more preferably 80% by mass or more, still more preferably 90% by mass or more, and yet still more preferably 95% by mass or more, and 100% by mass or less.

[Rubber Composition]

The rubber composition of the present invention contains the aforementioned lignin of the present invention, a rubber, and an inorganic filler.

From the viewpoint of improving the abrasion resistance, the content of lignin of the present invention is preferably 0.5 parts by mass or more, more preferably 0.75 parts by mass or more, still more preferably 1 part by mass or more, yet still more preferably 1.5 parts by mass or more, even yet still more preferably 2.5 parts by mass or more, and even still more preferably 3 parts by mass or more, and preferably 30 parts by mass or less, more preferably 25 parts by mass or less, still more preferably 18 parts by mass or less, and yet still more preferably 10 parts by mass or less based on 100 parts by mass of the rubber.

[Rubber]

From the viewpoint of making the effect of abrasion resistance improvement remarkable, the rubber is preferably at least one selected from a natural rubber and a diene-based synthetic rubber.

Examples of the diene-based synthetic rubber include a polyisoprene synthetic rubber (IR), a polybutadiene rubber (BR), a styrene-butadiene rubber (SBR), an acrylonitrile butadiene rubber (NBR), a chloroprene rubber (CR), a butyl rubber (IIR), and the like. The natural rubber or the diene-based synthetic rubber may be used alone, or may be used in combination of two or more thereof.

The content of the rubber is preferably 20% by mass or more, more preferably 25% by mass or more, still more preferably 30% by mass or more, yet still more preferably 44% by mass or more, and even yet still more preferably 50% by mass or more, and preferably 80% by mass or less, more preferably 70% by mass or less, and still more preferably 60% by mass or less in the rubber composition.

[Inorganic Filler]

As the inorganic filler, at least one selected from silica, aluminum hydroxide, clay, talc, calcium carbonate, and zeolite is exemplified. From the viewpoint of keeping wet grip property or rubber physical property satisfactory, the inorganic filler is preferably at least one selected from silica and aluminum hydroxide, and more preferably silica.

When the rubber composition contains silica, excellent storage elastic modulus and tan δ can be exhibited. In addition, when the rubber composition contains silica, the fuel-saving performance can be enhanced.

The silica does not refer to only silicon dioxide in a narrow sense but means a silicic acid-based filler.

The silica is at least one selected from silicic anhydride, hydrated silicic acid, and a silicic acid salt.

Examples of the silicic acid salt include calcium silicate, aluminum silicate, and the like.

The content of the inorganic filler in the rubber composition is preferably 5 parts by mass or more, more preferably 10 parts by mass or more, still more preferably 20 parts by mass or more, and yet still more preferably 50 parts by mass or more, and preferably 140 parts by mass or less, more preferably 90 parts by mass or less, and still more preferably 70 parts by mass or less based on 100 parts by mass of the rubber.

From the viewpoint of an effect for improving the abrasion resistance of lignin of the present invention, the content of lignin in the rubber composition is preferably 1 part by mass or more, more preferably 1.5 parts by mass or more, still more preferably 2 parts by mass or more, and yet still more preferably 5 parts by mass or more, and preferably 55 parts by mass or less, preferably 46 parts by mass or less, more preferably 33 parts by mass or less, still more preferably 19 parts by mass or less, and yet still more preferably 17 parts by mass or less based on 100 parts by mass of the inorganic filler.

Examples of other filler include carbon black and the like. As the carbon black, a known carbon back in which ranges of $I_2$ adsorption amount, CTAB specific surface area, $N_2$ adsorption amount, DBP adsorption amount, and so on are properly chosen can be used so long as it enhances the dynamic performance and improves the processability or the like. As for the kind of the carbon black, for example, those which are known, such as SAF, ISAF, HAF, etc., can be properly selected and used.

[Silane Coupling Agent]

It is preferred that the rubber composition of the present invention is further compounded with a silane coupling agent.

As for the silane coupling agent, an arbitrary material among conventionally known silane coupling agents can be used. Above all, at least one selected from a compound represented by the following general formula (4a), a compound represented by the following general formula (4b), a compound represented by the following general formula (4c), and a compound represented by the following general formula (4d) is preferred.

$$A_aB_{3-a}Si-X-S_b-X-SiA_aB_{3-a} \quad (4a)$$

In the formula, A represents an alkoxy group having a carbon number of 1 or more and 3 or less or a chlorine atom; B represents an alkyl group having a carbon number of 1 or more and 3 or less; X represents an alkane diyl group or an alkene diyl group each having a carbon number of 1 or more and 9 or less, or an arylene group having a carbon number of 7 or more and 15 or less; a is an integer of 1 or more and 3 or less; and b is an integer of 1 or more and 6 or less and may have a distribution, provided that when a is 1, then two Bs may be the same as or different from each other, and when a is 2 or 3, then two or three As may be the same as or different from each other.

$$A_aB_{3-a}Si-X-Y \quad (4b)$$

In the formula, A, B, X, and a are the same as mentioned above; and Y represents a mercapto group, a vinyl group, an amino group, a glycidoxy group, or an epoxy group.

$$A_aB_{3-a}Si-S_b-Z \quad (4c)$$

In the formula, A, B, X, a, and b are the same as mentioned above; and Z represents a benzothiazolyl group, an N,N-dimethylthiocarbamoyl group, a methacryloyl group, or a saturated or unsaturated hydrocarbon group a carbon number of having 1 or more and 15 or less.

$$A_cB_dD_eSi-X-S-CO-X^1 \quad (4d)$$

In the formula, A, B, and X are the same as mentioned above; $X^1$ represents a saturated or unsaturated alkyl group having a carbon number of 1 or more and 20 or less or an arene diyl group having a carbon number of 6 or more and 15 or less; D represents A, B, or an $-[O(XO)_n]_{0.5}$ group; n is an integer of 1 or more and 4 or less and may have a distribution; X is the same as mentioned above; and c, d, and e are numbers satisfying the relations of (0≤c≤3), (0≤d≤2), (0≤e≤1), and (c+d+2e=3), respectively.

Examples of the silane coupling agent represented by the general formula (4a) include bis(3-triethoxysilylpropyl)tetrasulfide, bis(3-trimethoxysilylpropyl)tetrasulfide, bis(3-methyldimethoxysilylpropyl)tetrasulfide, bis(3-triethoxysilylethyl)tetrasulfide, bis(3-triethoxysilylpropyl)disulfide, bis(3-trimethoxysilylpropyl)disulfide, bis(3-triethoxysilylpropyl)trisulfide, and the like.

Examples of the silane coupling agent represented by the general formula (4b) include 3-mercaptopropyltrimethoxysilane, 3-mercaptopropyltriethoxysilane, vinyltriethoxysilane, vinyltrimethoxysilane, 3-aminopropyltriethoxysilane, 3-aminopropyltrimethoxysilane, 3-mercaptopropylmethyldimethoxysilane, 3-glycidoxypropyltrimethoxysilane, 3-glycidoxypropylmethyldiethoxysilane, and the like.

Examples of the silane coupling agent represented by the general formula (4c) include 3-trimethoxysilylpropyl-N,N-dimethylcarbamoyl tetrasulfide, 3-trimethoxysilylpropyl-benzothiazolyl tetrasulfide, 3-trimethoxysilylpropylmethacryloyl monosulfide, 3-triethoxysilylpropyl-n-octyl disulfide, and the like.

Examples of the silane coupling agent represented by the general formula (4d) include 3-octanoylthiopropyltriethoxysilane and the like.

The silane coupling agent may be used alone, or may be used in combination of two or more thereof.

The amount of the silane coupling agent is preferably 1% by mass or more, and more preferably 3% by mass or more, and preferably 20% by mass or less, and more preferably 15% by mass or less relative to the amount of the inorganic filler.

In the rubber composition, if desired, various compounding agents which are typically used in the rubber industry, for example, a vulcanizing agent, a vulcanization accelerator, an antiaging agent, a scorch retarder, a softening agent, zinc white, stearic acid, etc., can be contained within a range where the object of the present invention is not hindered.

A method of adding the abrasion resistance improver for rubber composition of the present invention, the inorganic filler, such as silica, etc., other filler, the silane coupling agent, and the various additives to the rubber composition is not particularly limited, and the addition/mixing can be conducted using a kneading machine which is general for rubber, such as a Banbury mixer, a roll, an intensive mixer, etc.

The thus-obtained rubber composition of the present invention can be used as a member of a tire, and in particular, it is suitably useful as the member for a tread or a tread base.

A pneumatic tire is produced using the rubber composition of the present invention by a usual method. That is, as the need arises, the rubber composition of the present invention, in which the various chemicals are contained as mentioned above, is subjected in an unvulcanized stage to extrusion processing into a tread member, which is then subjected to sticking and molding on a tire molding machine by a usual method, whereby a green tire is molded. This green tire is heated and pressurized in a vulcanization machine, thereby obtaining a tire.

More specifically, the kneading is conducted using a mixer in a first kneading step and a second kneading step in this order, thereby preparing an unvulcanized rubber composition. In the first kneading step, the abrasion resistance improver for rubber composition in the present invention, an inorganic filler, such as silica, etc., a fatty acid, other filler, such as carbon black, etc., a silane coupling agent, and the like are kneaded in the aforementioned natural rubber and diene-based synthetic rubber. After thorough kneading, in the second kneading step, a vulcanizing agent, a vulcanization accelerator, an antiaging agent, a scorch retarder, a softening agent, zinc white, and so on are kneaded. A maximum temperature at the time of kneading of the rubber composition in the first kneading step is set to 165° C. or lower, and a maximum temperature at the time of kneading of the rubber composition in the second kneading step is set to 110° C. or lower. The obtained unvulcanized rubber composition is processed and molded as mentioned above, and then heated at 130° C. or higher and 180° C. or lower, whereby a vulcanized rubber can be formed.

With respect to the aforementioned embodiments, the present invention further discloses the following abrasion resistance improver for inorganic filler-containing rubber composition, rubber composition, tire, and production method, and so on.

<1> An abrasion resistance improver for inorganic filler-containing rubber composition, including, as an active ingredient, lignin having an aldehyde yield rate by alkaline nitrobenzene oxidation of 12% by mass or more.

<2> The abrasion resistance improver for inorganic filler-containing rubber composition as set forth in <1>, wherein the aldehyde yield rate by alkaline nitrobenzene oxidation is preferably 12% by mass or more, more preferably 15% by mass or more, more preferably 16% by mass or more, still more preferably 17% by mass or more, yet still more preferably 18% by mass or more, even yet still more preferably 20% by mass or more, even still more preferably 22% by mass or more, and even still more further preferably 25% by mass or more, and preferably 60% by mass or less, more preferably 50% by mass or less, still more preferably 40% by mass or less, and yet still more preferably 30% by mass or less.

<3> The abrasion resistance improver for inorganic filler-containing rubber composition as set forth in <1> or <2>, wherein a weigh average molecular weight of lignin is preferably 500 or more, more preferably 1,000 or more, still more preferably 1,200 or more, and yet still more preferably 1,500 or more, and preferably 30,000 or less, more preferably 12,000 or less, still more preferably 10,000 or less, yet still more preferably 8,000 or less, even yet still more preferably 5,000 or less, even still more preferably 3,000 or less, even still more further preferably 2,700 or less, and even yet still more further preferably 2,200 or less.

<4> The abrasion resistance improver for inorganic filler-containing rubber composition as set forth in any of <1> to <3>, wherein the sulfur content in the lignin is preferably 1% by mass or less, more preferably 0.8% by mass or less, and still more preferably 0.5% by mass or less, and preferably 0.001% by mass or more, more preferably 0.005% by mass or more, and still more preferably 0.01% by mass or more.

<5> The abrasion resistance improver for inorganic filler-containing rubber composition as set forth in any of <1> to <4>, wherein the lignin is one obtained through a method including the following steps (A-1) to (A-3);

Step (A-1); a step of subjecting a plant-based biomass to an enzymatic saccharification treatment to obtain a saccharification residue;

Step (A-2); a step of subjecting the saccharification residue obtained in the step (A-1) to a heat treatment in a solvent including water and at least one selected from organic solvents having a solubility in water at 20° C. of 90 g/L or more, to obtain a heat treatment solution containing lignin; and Step (A-3); a step of subjecting the heat treatment solution obtained in the step (A-2) to solid-liquid separation to remove insoluble components, thereby obtaining the lignin.

<6> The abrasion resistance improver for inorganic filler-containing rubber composition as set forth in <5>, wherein the enzyme is preferably one or more selected from the group consisting of a cellulase and a hemicellulase; more preferably one or more selected from the group consisting of cellobiohydrolase, a β-glucosidase, endoglucanase, and a hemicellulase; and still more preferably one or more selected from the group consisting of cellobiohydrolase and endoglucanase.

<7> The abrasion resistance improver for inorganic filler-containing rubber composition as set forth in <5> or <6>, wherein the enzyme is added in an amount of 0.001% (w/v) or more and 15% (w/v) or less to a substrate suspension of 0.5% (w/v) or more and 20% (w/v) or less.

<8> The abrasion resistance improver for inorganic filler-containing rubber composition as set forth in any of <5> to <7>, wherein the step (A-1) is conducted in a buffer solution having a pH of 2 or more and 10 or less.

<9> The abrasion resistance improver for inorganic filler-containing rubber composition as set forth in <8>, wherein the pH of the buffer solution is preferably 3 or more, and more preferably 4 or more, and preferably 7 or less, and more preferably 6 or less.

<10> The abrasion resistance improver for inorganic filler-containing rubber composition as set forth in any of <5> to <9>, wherein the step (A-1) is conducted under a condition at a reaction temperature of 10° C. or higher and 90° C. or lower.

<11> The abrasion resistance improver for inorganic filler-containing rubber composition as set forth in <10>, wherein the reaction temperature is preferably 20° C. or higher, and more preferably 40° C. or higher, and preferably 70° C. or lower, and more preferably 60° C. or lower.

<12> The abrasion resistance improver for inorganic filler-containing rubber composition as set forth in any of <5> to <11>, wherein the step (A-1) is conducted through a reaction for a reaction time of 30 minutes or more and 5 days or less.

<13> The abrasion resistance improver for inorganic filler-containing rubber composition as set forth in any of <5> to <12>, wherein the organic solvent used in the step (A-2) has a solubility in water at 20° C. of preferably 90 g/L or more, preferably 100 g/L or more, and more preferably 120 g/L or more.

<14> The abrasion resistance improver for inorganic filler-containing rubber composition as set forth in any of <5> to <13>, wherein the organic solvent used in the step (A-2) has an SP value of preferably 8 or more, and more preferably 9 or more, and preferably 23 or less, more preferably 16 or less, and still more preferably 13 or less.

<15> The abrasion resistance improver for inorganic filler-containing rubber composition as set forth in any of <5> to <14>, wherein the organic solvent used in the step (A-2) is preferably one or more selected from ethanol, isopropanol, 2-butanol, acetonitrile, dioxane, acetone, and methyl ethyl ketone; more preferably one or more selected from ethanol, isopropanol, 2-butanol, and acetone; and still more preferably acetone.

<16> The abrasion resistance improver for inorganic filler-containing rubber composition as set forth in any of <5> to <15>, wherein a ratio of the organic solvent and water in the solvent in the step (A-2) [(organic solvent)/water] (mass ratio) is preferably 90/10 to 0/100, more preferably 90/10 to 0.01/99.99, still more preferably 70/30 to 10/90, and yet still more preferably 60/40 to 40/60.

<17> The abrasion resistance improver for inorganic filler-containing rubber composition as set forth in any of <5> to <16>, wherein in the step (A-2), preferably, an acid or a base is further used, and more preferably an acid is further used.

<18> The abrasion resistance improver for inorganic filler-containing rubber composition as set forth in any of <5> to <17>, wherein the content of the acid or base is preferably 0.001% by mass or more, and more preferably 0.01% by mass or more, and preferably 1.0% by mass or less, and more preferably 0.5% by mass or less relative to the solvent in the step (A-2).

<19> The abrasion resistance improver for inorganic filler-containing rubber composition as set forth in any of <5> to <18>, wherein the use amount of the solvent in the step (A-2) is preferably 2 times by mass or more, more preferably 5 times by mass or more, still more preferably 10 times by mass or more, and yet still more preferably 15 times by mass or more, and preferably 40 times by mass or less, and more preferably 30 times by mass or less relative to the solid component of the saccharification residue.

<20> The abrasion resistance improver for inorganic filler-containing rubber composition as set forth in any of <5> to <19>, wherein the content of the organic solvent in the solvent in the step (A-2) is preferably 10% by mass or more, more preferably 30% by mass or more, and still more preferably 40% by mass or more, and preferably 90% by mass or less, more preferably 70% by mass or less, and still more preferably 60% by mass or less.

<21> The abrasion resistance improver for inorganic filler-containing rubber composition as set forth in any of <5> to <20>, wherein a heat treatment temperature in the step (A-2) is preferably 80° C. or higher, more preferably 100° C. or higher, still more preferably 120° C. or higher, and yet still more preferably 150° C. or higher, and preferably 280° C. or lower, more preferably 250° C. or lower, still more preferably 220° C. or lower, and yet still more preferably 200° C. or lower.

<22> The abrasion resistance improver for inorganic filler-containing rubber composition as set forth in any of <5> to <21>, wherein a pressure at the time of heat treatment in the step (A-2) is preferably 0.1 MPa or more, and more preferably 0.5 MPa or more, and preferably 15 MPa or less, more preferably 10 MPa or less, still more preferably 5 MPa or less, and yet still more preferably 3 MPa or less.

<23> The abrasion resistance improver for inorganic filler-containing rubber composition as set forth in any of <5> to <22>, wherein a time of the heat treatment in the step (A-2) is preferably 1 minute or more, more preferably 2 minutes or more, and still more preferably 10 minutes or more, and preferably 5 hours or less, more preferably 3 hours or less, still more preferably 2 hours or less, and yet still more preferably 1 hour or less.

<24> The abrasion resistance improver for inorganic filler-containing rubber composition as set forth in any of <5> to <23>, wherein the lignin is one obtained through a method further including the following step (A-4);

Step (A-4): a step of taking out lignin with a low molecular weight from the lignin obtained in the step (A-3).

<25> The abrasion resistance improver for inorganic filler-containing rubber composition as set forth in any of <1> to <4>, wherein the lignin is one obtained through a method including the following steps (B-1) and (B-2):

Step (B-1): a step of treating a plant-based biomass with 8 parts by mass or more and 70 parts by mass or less of a basic compound and 10 parts by mass or more and 10,000 parts by mass or less of water based on 100 parts by mass of a solid component of the plant-based biomass under a condition in which an H-factor is 3,000 or less; and Step (B-2): a step of obtaining the lignin as a water-soluble component from the plant-based biomass having gone through the step (B-1).

<26> The abrasion resistance improver for inorganic filler-containing rubber composition as set forth in <25>, wherein the basic compound is preferably an alkali metal hydroxide or an alkaline earth metal hydroxide, more preferably an alkali metal hydroxide, still more preferably sodium hydroxide or potassium hydroxide, and yet still more preferably sodium hydroxide.

<27> The abrasion resistance improver for inorganic filler-containing rubber composition as set forth in <25> or <26>, wherein the amount of the basic compound in the step (B-1) is preferably 70 parts by mass or less, more preferably 60 parts by mass or less, still more preferably 55 parts by mass or less, yet still more preferably 50 parts by mass or less, even yet still more preferably 40 parts by mass or less, even still more preferably 30 parts by mass or less, and even still more further preferably 20 parts by mass or less, and preferably 8 parts by mass or more, and more preferably 10 parts by mass or more based on 100 parts by mass of the solid component of the plant-based biomass.

<28> The abrasion resistance improver for inorganic filler-containing rubber composition as set forth in any of <25> to <27>, wherein the amount of water in the step (B-1) is preferably 10 parts by mass or more, more preferably 150 parts by mass or more, still more preferably 250 parts by mass or more, yet still more preferably 350 parts by mass or more, even yet still more preferably 450 parts by mass or more, even still more preferably 550 parts by mass or more, even still more further preferably 650 parts by mass or more, and even yet still more further preferably 750 parts by mass or more, and preferably 8,000 parts by mass or less, more preferably 5,000 parts by mass or less, still more preferably 3,500 parts by mass or less, yet still more preferably 2,500 parts by mass or less, and even yet still more preferably 1,500 parts by mass or less based on 100 parts by mass of the solid component of the plant-based biomass.

<29> The abrasion resistance improver for inorganic filler-containing rubber composition as set forth in any of <25> to <28>, wherein in the treatment of the step (B-1), the H-factor is preferably 0.01 or more, more preferably 0.1 or more, still more preferably 1 or more, yet still more preferably 2 or more, and even yet still more preferably 3 or more, and preferably 3,000 or less, more preferably 1,500 or less, still more preferably 1,200 or less, yet still more preferably 1,000 or less, even yet still more preferably 400 or less, even still more preferably 300 or less, even still more further preferably 100 or less, even yet still more further preferably 50 or less, and even yet still more further preferably 30 or less.

<30> The abrasion resistance improver for inorganic filler-containing rubber composition as set forth in <29>, wherein the H-factor is expressed by the following equation (2):

$$HF=\int_0^t \exp(43.2-16115/T)dt \quad (2)$$

wherein, t is a time (h); T is an absolute temperature (K); and an integral range is 0 to t.

<31> The abrasion resistance improver for inorganic filler-containing rubber composition as set forth in any of <25> to <30>, wherein the lignin is one obtained through a method further including the following step (B-3):

Step (B-3): a step of taking out lignin with a low molecular weight from the lignin obtained in the step (B-2).

<32> The abrasion resistance improver for inorganic filler-containing rubber composition as set forth in any of <5> to <31>, wherein the plant-based biomass is preferably a herbaceous biomass.

<33> The abrasion resistance improver for inorganic filler-containing rubber composition as set forth in <32>, wherein the plant-based biomass is preferably a gramineous plant raw material, more preferably sugar cane bagasse, corn cob, or rice straw, and still more preferably sugar cane bagasse.

<34> The abrasion resistance improver for inorganic filler-containing rubber composition as set forth in any of <1> to <33>, wherein the content of lignin is preferably 50% by mass or more, more preferably 80% by mass or more, still more preferably 90% by mass or more, and yet still more preferably 95% by mass or more.

<35> A rubber composition containing lignin having an aldehyde yield rate by alkaline nitrobenzene oxidation of 12% by mass or more, a rubber, and an inorganic filler.

<36> The rubber composition as set forth in <35>, wherein the content of lignin is preferably 0.5 parts by mass or more, more preferably 0.75 parts by mass or more, still more preferably 1 part by mass or more, yet still more preferably 1.5 parts by mass or more, even yet still more preferably 2.75 parts by mass or more, and even still more preferably 3 parts by mass or more, and preferably 30 parts by mass or less, more preferably 25 parts by mass or less, still more preferably 18 parts by mass or less, and yet still more preferably 10 parts by mass or less based on 100 parts by mass of the rubber.

<37> The rubber composition as set forth in <35> or <36>, wherein the content of the rubber is preferably 20% by mass or more, more preferably 25% by mass or more, still more preferably 30% by mass or more, yet still more preferably 44% by mass or more, and even yet still more preferably 50% by mass or more, and preferably 80% by mass or less, more preferably 70% by mass or less, and still more preferably 60% by mass or less in the rubber composition.

<38> The rubber composition as set forth in any of <35> to <37>, wherein the inorganic filler is at least one selected from silica, aluminum hydroxide, clay, talc, calcium carbonate, and zeolite, preferably at least one selected from silica and aluminum hydroxide, and more preferably silica.

<39> The rubber composition as set forth in any of <35> to <38>, wherein the content of the inorganic filler in the rubber composition is preferably 5 parts by mass or more, more preferably 10 parts by mass or more, and still more preferably 20 parts by mass or more, and preferably 140 parts by mass or less, more preferably 90 parts by mass or less, and still more preferably 70 parts by mass or less based on 100 parts by mass of the rubber.

<40> The rubber composition as set forth in any of <35> to <39>, wherein the content of lignin in the rubber composition is preferably 1 part by mass or more, more preferably 1.5 parts by mass or more, still more preferably 2 parts by mass or more, and yet still more preferably 5 parts by mass or more, and preferably 55 parts by mass or less, preferably 46 parts by mass or less, more preferably 33 parts by mass or less, still more preferably 19 parts by mass or less, and yet still more preferably 17 parts by mass or less based on 100 parts by mass of the inorganic filler.

<41> The rubber composition as set forth in any of <35> to <40>, wherein a silane coupling agent is further compounded.

<42> The rubber composition as set forth in <41>, wherein the amount of the silane coupling agent is preferably 1% by mass or more, and more preferably 3% by mass or more, and preferably 20% by mass or less, and more preferably 15% by mass or less relative to the amount of the inorganic filler.

<43> A tire using the rubber composition as set forth in any of <36> to <42>.

<44> A method for producing an abrasion resistance improver for inorganic filler-containing rubber composition, including, as an active ingredient, lignin having an aldehyde yield rate by alkaline nitrobenzene oxidation of 12% by mass or more, which includes the following steps (A-1) to (A-3):

Step (A-1): a step of subjecting a plant-based biomass to an enzymatic saccharification treatment to obtain a saccharification residue;

Step (A-2): a step of subjecting the saccharification residue obtained in the step (A-1) to a heat treatment in a solvent including water and at least one selected from organic solvents having a solubility in water at 20° C. of 90 g/L or more, to obtain a heat treatment solution containing lignin; and Step (A-3); a step of subjecting the heat treatment solution obtained in the step (A-2) to solid-liquid separation to remove insoluble components, thereby obtaining the lignin.

<45> A method for producing an abrasion resistance improver for inorganic filler-containing rubber composition, including, as an active ingredient, lignin having an aldehyde yield rate by alkaline nitrobenzene oxidation of 12% by mass or more, which includes the following steps (B-1) and (B-2);

Step (B-1); a step of treating a plant-based biomass with 8 parts by mass or more and 70 parts by mass or less of a basic compound and 10 parts by mass or more and 10,000 parts by mass or less of water based on 100 parts by mass of a solid component of the plant-based biomass under a condition in which an H-factor is 3,000 or less; and Step (B-2): a step of obtaining the lignin as a water-soluble component from the plant-based biomass having gone through the step (B-1).

<46> Use of lignin having an aldehyde yield rate by alkaline nitrobenzene oxidation of 12% by mass or more, for the purpose of improving abrasion resistance of an inorganic filler-containing rubber composition.

<47> Use of lignin having an aldehyde yield rate by alkaline nitrobenzene oxidation of 12% by mass or more, which is used for producing an inorganic filler-containing rubber composition having an effect for improving abrasion resistance.

<48> A method for improving abrasion resistance of a rubber composition, including mixing a rubber, an inorganic filler, and lignin having an aldehyde yield rate by alkaline nitrobenzene oxidation of 12% by mass or more.

EXAMPLES

In the following Examples and Comparative Examples, the measurement and evaluation of each of physical properties were conducted by the following methods.

<Aldehyde Yield Rate of Lignin by Alkaline Nitrobenzene Oxidation>

With respect to lignin or a reagent, a degree of denaturation of lignin was evaluated from an aldehyde yield rate thereof as an index using the alkaline nitrobenzene oxidation method described in a reference document ("Methods in Lignin Chemistry", UNI Publishing Co., Ltd., issued in 1994). Specifically, the degree of denaturation of lignin was measured by the following method.

50 mg of a lignin-containing sample was weighed. The lignin-containing sample, 7 mL of a 2M sodium hydroxide aqueous solution, and 0.4 mL of nitrobenzene were charged into a 20 mL vial and heated at 170° C. for 2.5 hours while stirring at 900 rpm. After completion of the reaction, the resulting reaction solution was cooled and then extracted with 10 mL of diethyl ether three times to remove a reduced product of nitrobenzene and an excess amount of nitrobenzene therefrom. Concentrated hydrochloric acid was added to the remaining water layer to adjust a pH value thereof to 1, and the obtained solution was extracted with 10 mL of diethyl ether three times. The resulting diethyl ether extraction solution was subjected to distillation under reduced pressure to obtain an oxidation mixture. The resulting mixture was diluted with 20 mL of dichloromethane in a measuring cylinder. Then, 2 mL of the obtained dilute solution was filtered through a Millipore HVHP membrane (available from Millipore Japan, pore size: 0.45 μm) and subjected to gas chromatography (GC).

The conditions for the gas chromatography were as follows. That is, a GC apparatus (available from Agilent Technologies Inc.) equipped with a column "Agilent J & W GC Column DB-5" (available from Agilent Technologies Inc.) was used under the following conditions: amount of the lignin-containing sample: 1.0 μL; helium flow rate; 10 mL/min; injection port temperature: 200° C.; split ratio: 10/1. The temperature condition was adjusted such that the reaction system was held at 60° C. for 1 minute, raised up to 60 to 250° C. at a rate of 5° C./min, and held at 250° C. for 10 minutes. The quantitative determination was conducted using a calibration curve prepared with respect to a peak area based on a concentration of respective reagents including vanillin, syringaldehyde, and p-hydroxybenzaldehyde, thereby determining a yield of each aldehyde produced in the sample.

The aldehyde yield rate (% by mass) was calculated according to the following equation and defined as an index of the degree of denaturation of lignin. It is expressed that the higher the aldehyde yield rate, the lower in denaturation the lignin.

Aldehyde yield rate(mass %)=(Aldehyde yield of a sum of aldehyde amounts of vanillin, syringaldehyde, and p-hydroxybenzaldehyde)/(Lignin mass of lignin in charged lignin-containing sample)×100

<Calculation of Lignin Content Ratio (Mass %) and Lignin Mass (g) in Lignin-Containing Sample>

The lignin content ratio and the lignin mass in the lignin-containing sample were calculated according to the following equations.

Lignin content ratio(mass %)=[{Acid-insoluble lignin content ratio(mass %)}+{Acid-soluble lignin content ratio(mass %)}]

Lignin mass(g)=[{Acid-insoluble lignin content ratio (mass %)}+{Acid-soluble lignin content ratio (mass %)}]×[{Collection amount of lignin-containing sample(on a dry basis)(g)}/100]

Here, the acid-insoluble lignin content ratio and the acid-soluble lignin content ratio were calculated by the following methods.

(Calculation of Acid-Insoluble Lignin Content Ratio)

The acid-insoluble lignin content ratio was calculated by subtracting an ash content in a crude acid-insoluble lignin according to the following equation.

Acid-insoluble lignin content ratio(mass %)={Crude acid-insoluble lignin content ratio(mass %)}× [100−{ash content(mass %)}]/100

(Calculation of Crude Acid-Insoluble Lignin Content Ratio)

A milled lignin-containing sample was dried under vacuum at 60° C. 300 mg of this dried lignin-containing sample was charged in a vial, 3 mL of 72% by mass sulfuric acid was added thereto, and the resulting mixture was properly stirred in a water bath at 30° C. for 1 hour. Thereafter, 84 mL of water was added thereto, and the resulting mixture was transferred into a pressure bottle and treated in an autoclave at 120° C. for 1 hour. Thereafter, the lignin-containing sample was taken out before its temperature was dropped to 70° C. or lower, and subjected to suction filtration using a 1G-3 glass filter whose constant weight was previously measured. The filtrate (A) was stored, whereas the glass filter attached with a residue was fully washed with water and then dried at 105° C. to measure a constant weight thereof, thereby determining a collection amount of the crude acid-insoluble lignin (on a dry basis).

Crude acid-insoluble lignin content ratio(mass %)= [{Mass of lignin residue(g)}/{Collection amount of lignin-containing sample(on a dry basis)(g)}]×100

(Calculation of Ash Content)

The crude acid-insoluble lignin was transferred into a crucible whose constant weight was previously measured, held therein at 575° C. for 12 hours, and then cooled to measure a constant weight of the crucible and determine a mass of the sample after ashing. The ash content was calculated according to the following equation.

Ash content(mass %)=[{Mass of sample after ashing (g)}/{Collection amount of crude acid-insoluble lignin(on a dry basis)(g)}]×100

(Calculation of Acid-Soluble Lignin Content Ratio)

The acid-soluble lignin was measured by the following method.

The filtrate (A) was sampled in a constant volume of 100 mL and measured for an absorbance thereof at 205 nm using a UV-Vis absorptiometer. At this time, the filtrate was properly diluted such that the absorbance thereof was 0.3 to 0.8.

Acid-soluble lignin content ratio(mass %)=$d×v×(As−Ab)/(a×w)×100$

Here, d: dilution ratio; v: constant volume (L) of filtrate; As: absorbance of sample solution; Ab: absorbance of blank solution; a: absorptivity coefficient of lignin; w: collection amount of sample (on a dry basis) (g).

As the absorptivity coefficient (a) of lignin, there was used 110 L/g/cm as the value described as the known average value in a reference document ("Methods in Lignin Chemistry", UNI Publishing Co., Ltd.).

<Sulfur Content in Lignin>

The sulfur content in the lignin-containing sample was calculated by the following ion chromatography.

[Analysis Operation]

About 0.02 to 0.05 g of the lignin-containing sample was collected in a combustion board, and tungsten oxide was added thereto. A combustion operation was conducted with an automated combustion system AQF-100 (available from Mitsubishi Chemical Corporation), and a sulfate ion was collected with an absorption solution (5 mL of 900 ppm hydrogen peroxide solution). The absorption solution was diluted with ion-exchanged water to make up constant 50 mL volume, thereby preparing a test solution. The test solution was measured by the ion chromatography, and the content of sulfur in the sample (conversion from sulfate ion: 0.3338) was calculated from the calibration curve.

[Operation Conditions of Combustion System]

Apparatus: Automated combustion system AQF-100 (available from Mitsubishi Chemical Corporation)

Maximum combustion temperature: 1,000° C.

Gas flow rate: Argon/oxygen: 200 mL/min, oxygen: 400 mL/min

Gas flow rate of water supply unit: Argon: 150 mL/min

[Ion Chromatography Operation Conditions]

Apparatus: ICS-1500 (available from DIONEX Corporation)

Detector: Conductivity detector

Separation column: IonPac AS12A (available from DIONEX Corporation)

Guard column: IonPac AG12A (available from DIONEX Corporation)

Eluting solution: Mixed solution of 2.7 mmol/L sodium carbonate and 0.3 mmol/L sodium hydrogen carbonate (1/1)

Flow rate of eluting solution: 1.5 mL/min

Suppressor: AERS 500 4-mm (recycle mode) (available from Thermo Fisher Scientific Inc.)

<Weight Average Molecular Weight of Lignin>

The molecular weight of lignin produced according to the present method was measured by means of gel permeation chromatography (hereafter also referred to as "GPC") under the following conditions.

[GPC Operation]

100 µL of the lignin-containing sample solution (1 mg/mL) was injected and measured. The molecular weight of the sample was calculated based on a calibration curve which was previously prepared.

[GPC Conditions]

Apparatus: HLC-8120GPC (available from Tosoh Corporation)

Detector: RI detector

Separation column: Two columns of TSK-GEL α-M (available from Tosoh Corporation)

Guard column: TSKgel guardcolumn α (available from Tosoh Corporation)

Column temperature: 40° C.

Eluting solution: N,N-Dimethylformamide solution having 60 mmol/L of $H_3PO_4$ and 50 mmol/L of LiBr added thereto Flow rate of eluting solution: 1 mL/min Standard sample: Monodisperse polystyrene mixed solution [A-500 (molecular weight: $5.0 \times 10^2$), F-10 (molecular weight: $9.64 \times 10^4$), and F-850 (molecular weight: $8.42 \times 10^6$), all of which are available from Tosoh Corporation; and those monodisperse polystyrenes available from Pressure Chemical (molecular weights: $4.0 \times 10^3$, $3.0 \times 10^4$, and $9.29 \times 10^5$)

<Preparation of Unvulcanized Rubber Composition>

In each of compounding compositions shown in the following tables, the components other than zinc white, a vulcanization accelerator, and sulfur were kneaded with a 60-mL closed-type mixer for 3 to 6 minutes, and when the temperature reached 165° C., the kneaded mixture was discharged to obtain a rubber composition. Here, after the rubber composition was cooled to 50° C. or lower, zinc white, a vulcanization accelerator, and sulfur were subsequently added to the rubber composition and kneaded for 3 minutes, and when the temperature reached 90° C. to 95° C., the kneaded mixture was discharged to obtain an unvulcanized rubber composition.

<Preparation of Vulcanized Rubber Test Piece for Measurement of Abrasion Resistance>

In conformity with JIS K6264-2, the above-obtained unvulcanized rubber composition was packed in a disk-like die having a thickness of 12.7 mm and a diameter of 63.5 mm and subjected to a vulcanization treatment at 160° C. to prepare a vulcanized rubber test piece.

<Preparation of Vulcanized Rubber Test Piece for Measurement of tan δ>

The above-obtained unvulcanized rubber composition was put between two sheets of SUS plate together with a metal-made frame having a thickness of 2 mm and 12 cm in square and subjected to a vulcanization treatment at 160° C. to a vulcanized rubber test piece.

<Vulcanization Time>

As for the vulcanization time of the aforementioned two test pieces, a vulcanization time (T90) of the unvulcanized rubber at 160° C. was determined in conformity with the vulcanization test with a vibration type vulcanization machine described in JIS K6300-2, and the vulcanization was conducted for a time obtained by multiplying T90 by 1.5.

<Measurement of Abrasion Resistance>

Using the vulcanized rubber test piece for measurement of abrasion resistance, the abrasion resistance was evaluated by an akron abrasion tester in conformity with JIS K6264-2. In the abrasion test, an abrasion rate at room temperature of 23° C., a load of 2,750 g, an angle of 15°, and 8,000 rpm was determined according to the following equation (II). In addition, an abrasion index was determined according to the following equation (III) while defining an abrasion rate of a tire composition including the components other than lignin as 100. It is expressed that the smaller the abrasion index, the more excellent the abrasion resistance of the rubber.

Abrasion rate(mass %)=[{Mass of test piece before the test(g)}−{Mass of test piece after the test(g)}/{Mass of test piece before the test(g)}]×100  (II)

Abrasion index=[{Abrasion rate(mass %)}/{Abrasion rate of Comparative Example(mass %)}]×100  (III)

The calculation was made while defining Comparative Example 1 as 100 in Table 1; Comparative Example 5 as 100 in Table 2; and Comparative Example 6 as 100 in Table 3, respectively.

<Measurement of Fuel-Saving Property (Low Heat Build-Up)>

For the fuel-saving property (low heat build-up), tan δ that is an index of viscoelasticity evaluation was used. The vulcanized rubber test piece for measurement of tan δ was used, and the tan δ was measured under conditions at 50° C. and 10 Hz and at a strain of 0.01% to 10% using a rotational rheometer (available from TA Instruments). The fuel-saving property was determined according to the following equation (IV) while defining the tan δ of the tire composition including the components other than lignin (value when the strain was 0.1) as 100. It is expressed that the smaller the tan δ at 50° C., the more excellent the fuel-saving property of the rubber (low heat build-up).

Fuel-saving property index=[{tan δ(strain: 0.1)}/{tan δ of Comparative Example(strain: 0.1)}]×100  (IV)

The calculation was made while defining Comparative Example 1 as 100 in Table 1; Comparative Example 5 as 100 in Table 2; and Comparative Example 6 as 100 in Table 3, respectively.

Preparation Example 1: Lignin 1 (Low Denatured)

(Pretreatment)

Bagasse (strained lees of sugar cane; water content: 7.0% by mass) as a herbaceous biomass was placed in a vacuum dryer "VO-320" (available from Advantec Toyo Kaisha, Ltd.) and dried under reduced pressure in a nitrogen flow for 2 hours, thereby obtaining a dried bagasse having a water content of 2.0% by mass, a holocellulose content of 71.3% by mass, and a lignin content of 22.8% by mass.

100 g of the obtained dried bagasse and granular sodium hydroxide "TOSOH PEARL" (available from Tosoh Corporation) having a particle diameter of 0.7 mm in an amount of 4.4 g (corresponding to 0.25 mol per mol of AGU constituting the holocellulose) were charged into a batch-type vibration mill "MB-1" (available from Chuo Kakohki Co., Ltd.; total container capacity: 3.5 L; filled with SUS304-made rods with a circular shape in section having a diameter of φ30 mm and a length of 218 mm, at a filling ratio of 57% by volume), and subjected to a milling treatment for 2 hours, thereby obtaining a milled bagasse (cellulose I-type crystallinity: 14%; average particle diameter: 56.6 μm). The obtained milled bagasse in an amount of 100 g (expressed in terms of a dry raw material from which the basic compound was removed) was neutralized with 1.0 M hydrochloric acid.

[Step (A-1)]

100 g of the obtained milled bagasse was put into 2.0 L of a 100 mM acetic acid buffer solution (pH: 5.0), and 20 mL of a cellulase/hemicellulase preparation "Cellic CTec 2" (available from Novozymes) was added thereto. The resulting mixture was held at 50° C. while stirring at 600 rpm to undergo enzymatic saccharification. After 24 hours, the reaction was terminated, and the resulting reaction solution was centrifuged to separate the solution into a supernatant and a saccharification residue. The saccharification residue was subjected to washing and centrifugation repeatedly, followed by freeze-drying.

[Step (A-2)]

The obtained saccharification residue (absolute dry mass: 250 mg) was charged into a reaction vessel (capacity: 5 mL), and 4.8 g of a mixed solvent of acetone/water (mass ratio: 50/50) and 240 μL of hydrochloric acid (concentration: 1.0 M) were added thereto. Then, the reaction vessel was hermetically closed, and the contents of the reaction vessel were subjected to microwave heating at 160° C. and 1.6 MPa for 30 minutes while stirring at 900 rpm using a microwave heater "Initiator 60" (available from Biotage Japan Ltd.), thereby obtaining a heat treatment solution.

[Step (A-3)]

The heat treatment solution obtained in the step (A-2) was centrifuged to separate the solution into an extraction solution and a residue. The resulting residue was washed with acetone, water, and a mixed solvent of acetone/water until an extraction solution therefrom became transparent. The extraction solutions obtained through the centrifugation and washing were gathered, to which was then added 240 μL of 1.0 M sodium hydroxide to undergo neutralization, and the solvent included in the extraction solution was then distilled off under reduced pressure. The resulting solid was again washed with water, and the obtained water-insoluble component was dried under reduced pressure at room temperature, thereby obtaining Lignin 1. An aldehyde yield rate of Lignin 1 by alkaline nitrobenzene oxidation was 20.1% by mass. A weight average molecular weight of Lignin 1 was 9,300. A sulfur content of Lignin 1 was 0.066% by mass. A lignin content ratio of Lignin 1 was 95% by mass.

Preparation Example 2: Lignin 2 (Low Denatured)

[Step (B-1)]

Bagasse as a herbaceous biomass in a dry mass of 30 g was placed in a glass bottle, and a 1.6% by mass sodium hydroxide aqueous solution was added thereto such that the solid component concentration was 10% by mass. The glass bottle was heated in an autoclave (LSX-700, available from Tomy Seiko Co., Ltd.) at 120° C. for 2 hours (H-factor: 20.3).

[Step (B-2)]

The reaction product obtained in the step (B-1) was filtered under reduced pressure using a 400-mesh SUS mesh and a Nutsche filter. The residue was washed with 300 mL of ion-exchanged water at 90° C. The filtrate and the washing solution were gathered, and 2.4 L of methanol (a special grade, available from Wako Pure Chemical Industries, Ltd.) was added thereto. A deposit was filtered under reduced pressure (with Filter Paper No. 2, available from Toyo Roshi Kaisha, Ltd.), and the methanol was distilled off under reduced pressure from the filtrate and then regulated with 1.0 M hydrochloric acid to a pH of 4.

The obtained suspension was centrifuged ("CR 20GIII", available from Hitachi Koki Co., Ltd., at 10,000 rpm for 20 minutes). A supernatant was removed, 300 mL of ion-exchanged water was added to the residue, and after stirring, the resultant was again centrifuged, followed by water washing. The water washing was conducted two times, and the obtained precipitate was subjected to freeze-drying to obtain Lignin 2. An aldehyde yield rate of Lignin 2 by alkaline nitrobenzene oxidation was 23.3% by mass. A weight average molecular weight of Lignin 2 was 7,600. A sulfur content of Lignin 2 was 0.11% by mass. A lignin content ratio of Lignin 2 was 99% by mass.

Preparation Example 3: Highly Denatured Lignin

Highly denatured lignin was obtained under the same conditions as in Preparation Example 2, except that in the step 1 of Preparation Example 2, a high pressure decomposition reaction vessel "HU50" (available from SAN-AI Kagaku Co., Ltd.) was used in place of the glass bottle, and heating was conducted with a vacuum dryer at a temperature 170° C. for a time of 6 hours (H-factor: 5,800). An aldehyde yield rate of the highly denatured lignin by alkaline nitrobenzene oxidation was 8.7% by mass. A weight average molecular weight of the highly denatured lignin was 7,100. A sulfur content of the highly denatured lignin was 0.10% by mass. A lignin content ratio of the highly denatured lignin was 90% by mass.

Preparation Example 4: Lignin 3 (Low Denatured)

10 g of the lignin obtained in Preparation Example 1 was weighed in a 1,000-mL Erlenmeyer flask, 100 mL of ethyl acetate was added thereto, and the resulting mixture was stirred for 3 hours, followed by solvent extraction. Thereafter, the extract was subjected to solid-liquid separation with a filter paper "Filter Paper No. 2" (available from Toyo Roshi Kaisha, Ltd.). The ethyl acetate was distilled off under reduced pressure from the filtrate, thereby obtaining 3 g of Lignin 3. An aldehyde yield rate of Lignin 3 by alkaline nitrobenzene oxidation was 20.4% by mass. A weight average molecular weight of Lignin 3 was 1,300. A sulfur content of Lignin 3 was 0.028% by mass. A lignin content ratio of Lignin 3 was 95% by mass.

Preparation Example 5: Lignin 4 (Low Denatured)

10 g of the lignin obtained in Preparation Example 2 was weighed in a 1,000-mL Erlenmeyer flask, a mixed solvent of methanol/water (mass ratio: 50/50) was added thereto, and the resulting mixture was stirred for 3 hours, followed by solvent extraction. Thereafter, the extract was subjected to solid-liquid separation with a filter paper "Filter Paper No. 2" (available from Toyo Roshi Kaisha, Ltd.). The methanol and water were distilled off under reduced pressure from the filtrate, thereby obtaining 1 g of Lignin 4. An aldehyde yield rate of Lignin 4 by alkaline nitrobenzene oxidation was 19.8% by mass. A weight average molecular weight of Lignin 4 was 2,000. A sulfur content of Lignin 4 was 0.14% by mass. A lignin content ratio of Lignin 4 was 98% by mass.

Preparation Example 6: Lignin 5 (Low Denatured)

[Step (B-1)]

Bagasse as a herbaceous biomass in a dry mass of 30 g was placed in a glass bottle, and a 1.6% by mass sodium hydroxide aqueous solution was added thereto such that the solid component concentration was 10% by mass. The glass bottle was heated in a thermostat at 95° C. for 6 hours (H-factor: 3.5).

[Step (B-2)]

The reaction product obtained in the step (B-1) was filtered under reduced pressure using a 400-mesh SUS mesh and a Nutsche filter. The residue was washed with 300 mL of ion-exchanged water at 90° C. The filtrate and the washing solution were gathered, and 2.4 L of methanol (a special grade, available from Wako Pure Chemical Industries, Ltd.) was added thereto. A deposit was filtered under reduced pressure (with Filter Paper No. 2, available from Toyo Roshi Kaisha, Ltd.), and the methanol was distilled off under reduced pressure from the filtrate and then regulated with 1.0 M hydrochloric acid to a pH of 4.

The obtained suspension was centrifuged ("CR 20GIII", available from Hitachi Koki Co., Ltd., at 10,000 rpm for 20 minutes). A supernatant was removed, 300 mL of ion-exchanged water was added to the residue, and after stirring, the resultant was again centrifuged, followed by water washing. The water washing was conducted two times, and the obtained precipitate was subjected to freeze-drying.

[Step (B-3)]

To the obtained lignin, 1,000% by mass of a mixed solvent of methanol/water (mass ratio: 50/50) was added, and the resulting mixture was stirred for 3 hours, followed by solvent extraction. Thereafter, the extract was subjected to solid-liquid separation with a filter paper "Filter Paper No. 2" (available from Toyo Roshi Kaisha, Ltd.). The methanol and water were distilled off under reduced pressure from the filtrate, thereby obtaining Lignin 5. An aldehyde yield rate of Lignin 5 by alkaline nitrobenzene oxidation was 27.4% by mass. A weight average molecular weight of Lignin 5 was 2,200. A sulfur content of Lignin 5 was 0.13% by mass. A lignin content ratio of Lignin 5 was 81% by mass.

Preparation Example 7: Lignin 6 (Low Denatured)

Lignin 7 was obtained under the same conditions as in Preparation Example 6, except that in the step (B-3) of Preparation Example 6, the extraction solvent was changed to acetone in place of the mixed solvent of methanol/water (mass ratio: 50/50). An aldehyde yield rate of Lignin 7 by alkaline nitrobenzene oxidation was 27.3% by mass. A weight average molecular weight of Lignin 6 was 1,700. A sulfur content of Lignin 6 was 0.085% by mass. A lignin content ratio of Lignin 6 was 95% by mass.

Preparation Example 8: Lignin 7 (Low Denatured)

[Step (B-1)]

Bagasse as a herbaceous biomass in a dry mass of 30 g was placed in a glass bottle, and a 1.6% by mass sodium hydroxide aqueous solution was added thereto such that the solid component concentration was 10% by mass. The glass bottle was heated in an autoclave (LSX-700, available from Tomy Seiko Co., Ltd.) at 120° C. for 24 hours (H-factor: 216).

[Step (B-2)]

The reaction product obtained in the step (B-1) was filtered under reduced pressure using a 400-mesh SUS mesh and a Nutsche filter. The residue was washed with 300 mL of ion-exchanged water at 90° C. The filtrate was regulated with 1.0 M hydrochloric acid to a pH of 4.

The obtained suspension was centrifuged ("CR 20GIII", available from Hitachi Koki Co., Ltd., at 10,000 rpm for 20 minutes). A supernatant was removed, 300 mL of ion-exchanged water was added to the residue, and after stirring, the resultant was again centrifuged, followed by water washing. The water washing was conducted two times, the obtained precipitate was subjected to freeze-drying.

[Step (B-3)]

To the obtained lignin, 1,000% by mass of acetone was added, and the resulting mixture was stirred for 3 hours, followed by solvent extraction. Thereafter, the extract was subjected to solid-liquid separation with a filter paper "Filter Paper No. 2" (available from Toyo Roshi Kaisha, Ltd.). The acetone was distilled off under reduced pressure from the filtrate, thereby obtaining Lignin 7. An aldehyde yield rate of Lignin 7 by alkaline nitrobenzene oxidation was 12.6% by mass. A weight average molecular weight of Lignin 7 was 2,600. A sulfur content of Lignin 7 was 0.065% by mass. A lignin content ratio of Lignin 7 was 93% by mass.

Examples 1 to 10 and Comparative Examples 1 to 6

Test pieces obtained through compounding of compositions shown in Tables 1 to 3 were prepared, and physical properties thereof were evaluated. The results are shown in Tables 1 to 3.

TABLE 1

| | | Example 1 | Example 2 | Example 3 | Example 4 | Example 5 | Example 6 | Example 7 | Comparative Example 1 | Comparative Example 2 | Comparative Example 3 | Comparative Example 4 |
|---|---|---|---|---|---|---|---|---|---|---|---|---|
| Rubber composition (parts by mass) | S-SBR *1 | 100 | 100 | 100 | 100 | 100 | 100 | 100 | 100 | 100 | 100 | 100 |
| | Lignin 1 *2 | 10 | | | | | | | | | | |
| | Lignin 2 *3 | | 10 | | | | | | | | | |
| | Lignin 3 *4 | | | 10 | | | | | | | | |
| | Lignin 4 *5 | | | | 10 | | | 3 | | | | |
| | Lignin 5 *6 | | | | | 10 | | | | | | |
| | Lignin 6 *7 | | | | | | 10 | | | | | |
| | Lignin 7 *8 | | | | | | | | | | | |
| | Highly denatured lignin *9 | | | | | | | | | 10 | | |
| | Commercially available highly denatured lignin 1 *10 | | | | | | | | | | 10 | |
| | Commercially available highly denatured lignin 2 *11 | | | | | | | | | | | 10 |
| | Carbon black *12 | 5 | 5 | 5 | 5 | 5 | 5 | 5 | 5 | 5 | 5 | 5 |
| | Silica *13 | 55 | 55 | 55 | 55 | 55 | 55 | 55 | 55 | 55 | 55 | 55 |
| | Silane coupling agent *14 | 5.5 | 5.5 | 5.5 | 5.5 | 5.5 | 5.5 | 5.5 | 5.5 | 5.5 | 5.5 | 5.5 |
| | Stearic acid *15 | 2 | 2 | 2 | 2 | 2 | 2 | 2 | 2 | 2 | 2 | 2 |
| | Oil | | | | | | | | | | | |
| | Zinc white *16 | 3 | 3 | 3 | 3 | 3 | 3 | 3 | 3 | 3 | 3 | 3 |
| | Vulcanization accelerator D *17 | 1 | 1 | 1 | 1 | 1 | 1 | 1 | 1 | 1 | 1 | 1 |
| | Vulcanization accelerator DM *18 | 1 | 1 | 1 | 1 | 1 | 1 | 1 | 1 | 1 | 1 | 1 |
| | Vulcanization accelerator NS *19 | 0.5 | 0.5 | 0.5 | 0.5 | 0.5 | 0.5 | 0.5 | 0.5 | 0.5 | 0.5 | 0.5 |
| | Sulfur *20 | 1.5 | 1.5 | 1.5 | 1.5 | 1.5 | 1.5 | 1.5 | 1.5 | 1.5 | 1.5 | 1.5 |
| Lignin | Kind of lignin | Lignin 1 (low denatured) | Lignin 2 (low denatured) | Lignin 3 (low denatured) | Lignin 4 (low denatured) | Lignin 5 (low denatured) | Lignin 6 (low denatured) | Lignin 4 (low denatured) | None | Highly denatured lignin | Commercially available highly denatured lignin 1 | Commercially available highly denatured lignin 2 |
| | Lignin content ratio (mass %) | 95 | 99 | 95 | 98 | 81 | 95 | 98 | — | 90 | 84 | 85 |
| | Aldehyde yield rate (mass %) | 20.1 | 23.3 | 20.4 | 19.8 | 27.4 | 27.3 | 19.8 | — | 8.7 | 5.5 | 11 |
| | Weight average molecular weight (expressed in terms of polystyrene) | 9300 | 7600 | 1300 | 2000 | 2200 | 1700 | 2000 | — | 7100 | 14400 | >52000 Catalogue value |
| | Sulfur content of lignin (mass %) | 0.066 | 0.11 | 0.028 | 0.14 | 0.13 | 0.085 | 0.14 | — | 0.10 | 4.5 | 6.0 |
| Composition | Total amount | 184.5 | 184.5 | 184.5 | 184.5 | 184.5 | 184.5 | 177.5 | 174.5 | 184.50 | 184.50 | 184.50 |
| | Rubber content (mass %) | 54.2 | 54.2 | 54.2 | 54.2 | 54.2 | 54.2 | 56.3 | 57.3 | 54.2 | 54.2 | 54.2 |
| | Inorganic filler (silica)/rubber mass ratio | 0.55 | 0.55 | 0.55 | 0.55 | 0.55 | 0.55 | 0.55 | 0.550 | 0.550 | 0.550 | 0.550 |
| | Lignin/rubber ratio | 0.095 | 0.099 | 0.095 | 0.098 | 0.081 | 0.095 | 0.029 | — | 0.090 | 0.084 | 0.085 |
| | Lignin/silica ratio | 0.173 | 0.180 | 0.173 | 0.178 | 0.147 | 0.173 | 0.053 | — | 0.164 | 0.153 | 0.155 |
| Evaluation | Abrasion resistance | 83 | 95 | 95 | 86 | 88 | 85 | 82 | 100 | 117 | 124 | 107 |
| | tan δ (strain: 0.1%) | 106 | 91 | 90 | 90 | 93 | 87 | 105 | 100 | 80 | 97 | 98 |

TABLE 2

|  |  | Example 8 | Example 9 | Comparative Example 5 |
|---|---|---|---|---|
| Rubber composition (parts by mass) | S-SBR *1 | 100 | 100 | 100 |
|  | Lignin 1 *2 |  |  |  |
|  | Lignin 2 *3 |  |  |  |
|  | Lignin 3 *4 |  |  |  |
|  | Lignin 4 *5 |  |  |  |
|  | Lignin 5 *6 |  |  |  |
|  | Lignin 6 *7 | 2.75 |  |  |
|  | Lignin 7 *8 |  | 2.75 |  |
|  | Highly denatured lignin *9 |  |  |  |
|  | Commercially available highly denatured lignin 1 *10 |  |  |  |
|  | Commercially available highly denatured lignin 2 *11 |  |  |  |
|  | Carbon black *12 |  |  |  |
|  | Silica *13 | 55 | 55 | 55 |
|  | Silane coupling agent *14 | 5.5 | 5.5 | 5.5 |
|  | Stearic acid *15 | 2 | 2 | 2 |
|  | Oil |  |  |  |
|  | Zinc white *16 | 2.5 | 2.5 | 2.5 |
|  | Vulcanization accelerator D *17 | 1.4 | 1.4 | 1.4 |
|  | Vulcanization accelerator DM *18 | 2 | 2 | 2 |
|  | Vulcanization accelerator NS *19 | 0.7 | 0.7 | 0.7 |
|  | Sulfur *20 | 1.5 | 1.5 | 1.5 |
| Lignin | Kind of lignin | Lignin 6 (low denatured) | Lignin 7 (low denatured) | None |
|  | Lignin content ratio (mass %) | 95 | 93 | — |
|  | Aldehyde yield rate (mass %) | 27.3 | 12.6 | — |
|  | Weight average molecular weight (expressed in terms of polystyrene) | 1700 | 2600 | — |
|  | Sulfur content of lignin (mass %) | 0.085 | 0.065 | — |
| Composition | Total amount | 177.25 | 177.25 | 170.6 |
|  | Rubber content (mass %) | 56.0 | 56.0 | 58.6 |
|  | Inorganic filler (silica)/rubber mass ratio | 0.550 | 0.550 | 0.550 |
|  | Lignin/rubber ratio | 0.026 | 0.026 | — |
|  | Lignin/silica ratio | 0.048 | 0.047 | — |
| Evaluation | Abrasion resistance | 87 | 86 | 100 |
|  | tanδ (strain: 0.1%) | 96 | 97 | 100 |

TABLE 3

|  |  | Example 10 | Comparative Example 6 |
|---|---|---|---|
| Rubber composition (parts by mass) | S-SBR *1 | 100 | 100 |
|  | Lignin 1 *2 |  |  |
|  | Lignin 2 *3 |  |  |
|  | Lignin 3 *4 |  |  |
|  | Lignin 4 *5 |  |  |
|  | Lignin 5 *6 |  |  |
|  | Lignin 6 *7 | 3.25 |  |
|  | Lignin 7 *8 |  |  |
|  | Highly denatured lignin *9 |  |  |
|  | Commercially available highly denatured lignin 1 *10 |  |  |
|  | Commercially available highly denatured lignin 2 *11 |  |  |
|  | Carbon black *12 | 5 | 5 |
|  | Silica *13 | 65 | 65 |
|  | Silane coupling agent *14 | 6.5 | 6.5 |
|  | Stearic acid *15 | 2 | 2 |
|  | Oil | 10 | 10 |
|  | Zinc white *16 | 2.5 | 2.5 |
|  | Vulcanization accelerator D *17 | 1.4 | 1.4 |
|  | Vulcanization accelerator DM *18 | 2 | 2 |
|  | Vulcanization accelerator NS *19 | 0.7 | 0.7 |
|  | Sulfur *20 | 1.5 | 1.5 |
| Lignin | Kind of lignin | Lignin 6 (low denatured) | None |
|  | Lignin content ratio (mass %) | 95 | — |
|  | Aldehyde yield rate (mass %) | 27.3 | — |
|  | Weight average molecular weight | 1700 | — |

TABLE 3-continued

|  |  | Example 10 | Comparative Example 6 |
|---|---|---|---|
|  | (expressed in terms of polystyrene) Sulfur content of lignin (mass %) | 0.085 | — |
| Composition | Total amount | 177.75 | 196.6 |
|  | Rubber content (mass %) | 56.0 | 50.9 |
|  | Inorganic filler (silica)/rubber mass ratio | 0.650 | 0.650 |
|  | Lignin/rubber ratio | 0.031 | — |
|  | Lignin/silica ratio | 0.048 | — |
| Evaluation | Abrasion resistance | 90 | 100 |
|  | tanδ (strain: 0.1%) | 91 | 100 |

The details of the respective components shown in the tables are as follows.

*1: Solution-polymerized styrene/butadiene rubber, "NIPOL (a registered trademark) NS210", available from Zeon Corporation
*2: Lignin 1 obtained in Preparation Example 1
*3: Lignin 2 obtained in Preparation Example 2
*4: Lignin 3 obtained in Preparation Example 4
*5: Lignin 4 obtained in Preparation Example 5
*6: Lignin 5 obtained in Preparation Example 6
*7: Lignin 6 obtained in Preparation Example 7
*8: Lignin 7 obtained in Preparation Example 8
*9: Highly denatured lignin obtained in Preparation Example 3
*10: Lignin (dealkalized), "L0045", available from Tokyo Chemical Industry Co., Ltd.
*11: Sodium lignosulfonate, "471038-100G", available from Aldrich
*12: "SEAST 3", available from Tokai Carbon Co., Ltd.
*13: Precipitated silica (white carbon), "NIPSIL AQ", available from Tosoh Silica Corporation
*14: Bis(3-triethoxysilylpropyl)tetrasulfide, "Si69", available from Degussa
*15: "LUNAC S-70V", available from Kao Corporation
*16: "Zinc Oxide Wako 1st Grade", available from Wako Pure Chemical Industries, Ltd.
*17: Guanidine-based vulcanization accelerator, 1,3-diphenyl guanidine (DPG), "NOCCELER D", available from Ouchi Shinko Chemical Industrial Co., Ltd.
*18: Thiazole-based vulcanization accelerator, di-2-benzothiazyl disulfide (MBTS), "NOCCELER DM", available from Ouchi Shinko Chemical Industrial Co., Ltd.
*19: Sulfenamide-based vulcanization accelerator, N-tert-butyl-2-benzothiazyl sulfenamide (TBBS), "SANCELER NS", available from Sanshin Chemical Industry Co., Ltd.
*20: "Sulfur powder for chemical use", available from Wako Pure Chemical Industries, Ltd.

INDUSTRIAL APPLICABILITY

In accordance with the present invention, an abrasion resistance improver for inorganic filler-containing rubber composition capable of giving high abrasion resistance to a rubber composition containing an inorganic filler can be provided.

The invention claimed is:

1. A rubber composition comprising lignin having an aldehyde yield rate by alkaline nitrobenzene oxidation of 12% by mass or more, a rubber, and an inorganic filler.

2. The rubber composition according to claim 1, wherein the lignin has a weight average molecular weight of 500 or more and 30,000 or less.

3. The rubber composition according to claim 1, wherein the content of lignin is 0.5 parts by mass or more and 30 parts by mass or less based on 100 parts by mass of the rubber.

4. The rubber composition according to claim 1, wherein the inorganic filler is at least one selected from silica, aluminum hydroxide, clay, talc, calcium carbonate, and zeolite.

5. The rubber composition according to claim 1, wherein the content of the inorganic filler in the rubber composition is 5 parts by mass or more and 140 parts by mass or less based on 100 parts by mass of the rubber.

6. The rubber composition according to claim 1, wherein the content of lignin in the rubber composition is 1 part by mass or more and 55 parts by mass or less based on 100 parts by mass of the inorganic filler.

7. The rubber composition according to claim 1, wherein a silane coupling agent is further compounded.

8. The rubber composition according to claim 1, wherein the lignin is one obtained through a method comprising the following steps (A-1) to (A-3):
   Step (A-1): a step of subjecting a plant-based biomass to an enzymatic saccharification treatment to obtain a saccharification residue;
   Step (A-2): a step of subjecting the saccharification residue obtained in the step (A-1) to a heat treatment in a solvent including water and at least one selected from organic solvents having a solubility in water at 20° C. of 90 g/L or more, to obtain a heat treatment solution containing lignin; and
   Step (A-3): a step of subjecting the heat treatment solution obtained in the step (A-2) to solid-liquid separation to remove insoluble components, thereby obtaining the lignin.

9. The rubber composition according to claim 8, wherein the enzyme is one or more selected from the group consisting of a cellulase and a hemicellulase.

10. The rubber composition according to claim 1, wherein the lignin is one obtained through a method comprising the following steps (B-1) and (B-2):
   Step (B-1): a step of treating a plant-based biomass with 8 parts by mass or more and 70 parts by mass or less of a basic compound and 10 parts by mass or more and 10,000 parts by mass or less of water based on 100 parts by mass of a solid component of the plant-based biomass under a condition in which an H-factor is 3,000 or less; and Step (B-2): a step of obtaining the lignin as a water-soluble component from the plant-based biomass having gone through the step (B-1).

11. The rubber composition according to claim 10, wherein the basic compound is an alkali metal hydroxide or an alkaline earth metal hydroxide.

12. A tire using the rubber composition according to claim 1.

13. A method for improving abrasion resistance of a rubber composition, comprising mixing a rubber, an inorganic filler, and lignin having an aldehyde yield rate by alkaline nitrobenzene oxidation of 12% by mass or more.

14. The method for improving abrasion resistance of a rubber composition according to claim 13, wherein a weight average molecular weight of lignin is 500 or more and 30,000 or less.

15. The method for improving abrasion resistance of a rubber composition according to claim 13, wherein the content of lignin is 0.5 parts by mass or more and 30 parts by mass or less based on 100 parts by mass of the rubber.

16. The method for improving abrasion resistance of a rubber composition according to claim 13, wherein the content of the inorganic filler in the rubber composition is 5 parts by mass or more and 140 parts by mass or less based on 100 parts by mass of the rubber.

17. The method for improving abrasion resistance of a rubber composition according to claim 13, wherein the content of lignin in the rubber composition is 1 part by mass or more and 55 parts by mass or less based on 100 parts by mass of the inorganic filler.

18. The method for improving abrasion resistance of a rubber composition according to claim 13, wherein the inorganic filler is at least one selected from silica, aluminum hydroxide, clay, talc, calcium carbonate, and zeolite.

19. The method for improving abrasion resistance of a rubber composition according to claim 13, wherein a silane coupling agent is further compounded.

* * * * *